United States Patent
Kirchhofer et al.

(10) Patent No.: US 9,750,334 B2
(45) Date of Patent: Sep. 5, 2017

(54) TOOTHBRUSH WITH INJECTION-MOULDED BRISTLES AND METHOD AND APPARATUS FOR PRODUCING THE SAME

(75) Inventors: Roger Kirchhofer, Reitnau (CH); Peter Zurfluh, Alpnach (CH); Michael Schar, Egolzwil (CH)

(73) Assignee: TRISA HOLDING AG, Triengen (CH)

( * ) Notice: Subject to any disclaimer, the term of this patent is extended or adjusted under 35 U.S.C. 154(b) by 836 days.

(21) Appl. No.: 13/978,480

(22) PCT Filed: Jan. 3, 2012

(86) PCT No.: PCT/EP2012/000009
§ 371 (c)(1),
(2), (4) Date: Jul. 5, 2013

(87) PCT Pub. No.: WO2012/093085
PCT Pub. Date: Jul. 12, 2012

(65) Prior Publication Data
US 2013/0291320 A1    Nov. 7, 2013

(30) Foreign Application Priority Data
Jan. 4, 2011  (EP) .................................... 11000032

(51) Int. Cl.
A46B 3/00     (2006.01)
A46B 9/04     (2006.01)
(Continued)

(52) U.S. Cl.
CPC .................. *A46B 9/04* (2013.01); *A46B 1/00* (2013.01); *A46B 3/005* (2013.01); *A46B 3/04* (2013.01);
(Continued)

(58) Field of Classification Search
CPC .. A46B 1/00; A46B 3/005; A46D 3/00; A46D 3/005
See application file for complete search history.

(56) References Cited

U.S. PATENT DOCUMENTS 2,225,331 A   12/1940  Campbell
3,302,230 A   2/1967   Poppelman
(Continued)

FOREIGN PATENT DOCUMENTS

DE    18 62 043 U     11/1962
DE    102 35 642 A1   2/2004
(Continued)

OTHER PUBLICATIONS

U.S. Appl. No. 14/410,536, filed Dec. 22, 2014 in the name of Schär et al.
(Continued)

*Primary Examiner* — Randall Chin
(74) *Attorney, Agent, or Firm* — Oliff PLC

(57) ABSTRACT

The brush according to the invention has a bristle carrier, which is produced by injection molding, and bristles, which are produced from a bristle material likewise by injection molding. The bristle carrier is provided with at least one distributing channel for the bristle material. The bristles are formed integrally with the bristle material in the distribution channel.

35 Claims, 20 Drawing Sheets

(51) Int. Cl.
*A46D 3/00* (2006.01)
*A46B 1/00* (2006.01)
*A46B 3/04* (2006.01)
*A46B 3/22* (2006.01)
*A46B 9/06* (2006.01)
*A46D 1/00* (2006.01)
*A46B 15/00* (2006.01)
*A61C 17/22* (2006.01)

(52) U.S. Cl.
CPC ............... *A46B 3/22* (2013.01); *A46B 9/06* (2013.01); *A46B 15/0075* (2013.01); *A46D 1/00* (2013.01); *A46D 3/00* (2013.01); *A46D 3/005* (2013.01); *A61C 17/222* (2013.01)

(56) References Cited

U.S. PATENT DOCUMENTS

| | | | |
|---|---|---|---|
| 3,698,405 | A | 10/1972 | Walker |
| 4,635,313 | A * | 1/1987 | Fassler .............. A46B 3/04 15/193 |
| 5,497,526 | A * | 3/1996 | Klinkhammer ...... A46B 5/0012 132/309 |
| 5,775,346 | A | 7/1998 | Szyszkowski |
| 6,085,761 | A | 7/2000 | Inaba |
| 6,292,973 | B1 | 9/2001 | Moskovich et al. |
| 6,859,969 | B2 | 3/2005 | Gavney, Jr. et al. |
| 7,047,589 | B2 | 5/2006 | Gavney, Jr. |
| 7,182,542 | B2 | 2/2007 | Hohlbein |
| 7,281,768 | B2 * | 10/2007 | Sato .................. A46B 3/02 300/2 |
| D637,817 | S | 5/2011 | Smith |
| 8,109,686 | B2 * | 2/2012 | Bartschi .............. A46B 11/0003 401/132 |
| 8,851,781 | B2 * | 10/2014 | Bartschi .............. A46B 11/0003 401/132 |
| 8,893,344 | B2 * | 11/2014 | Boucherie .............. A46B 3/06 15/159.1 |
| 2003/0163884 | A1 | 9/2003 | Weihrauch |
| 2005/0006819 | A1 | 1/2005 | Weihrauch |
| 2005/0034740 | A1 | 2/2005 | Eckers et al. |
| 2005/0172439 | A1 | 8/2005 | Weihrauch |
| 2006/0085931 | A1 | 4/2006 | Roberts et al. |
| 2006/0230563 | A1 | 10/2006 | Gavney, Jr. |
| 2007/0101525 | A1 | 5/2007 | Hohlbein |
| 2009/0230756 | A1 | 9/2009 | Crossman |
| 2010/0024839 | A1 | 2/2010 | Kalbfeld et al. |

FOREIGN PATENT DOCUMENTS

| | | |
|---|---|---|
| EP | 0 952 571 A2 | 10/1999 |
| EP | 1 258 227 A2 | 11/2002 |
| EP | 1 911 414 A2 | 4/2008 |
| FR | 2 943 898 A3 | 10/2010 |
| WO | 98/16169 A1 | 4/1998 |
| WO | WO 02/28222 A1 | 4/2002 |
| WO | WO 03/079849 A1 | 10/2003 |
| WO | WO 2004/113047 A1 | 12/2004 |
| WO | WO 2007/005753 A2 | 1/2007 |
| WO | WO 2007/076405 A1 | 7/2007 |
| WO | WO 2008/135953 A1 | 11/2008 |
| WO | 2008/146968 A1 | 12/2008 |
| WO | WO 2009/072747 A1 | 6/2009 |

OTHER PUBLICATIONS

Nov. 12, 2013 International Search Report issued in International Patent Application No. PCT/EP2013/001412.
Oct. 10, 2012 International Search Report issued in International Patent Application No. PCT/EP2012/000009.
Jul. 10, 2013 International Preliminary Report on Patentability issued in International Patent Application No. PCT/EP2012/000009.
Nov. 17, 2016 Office Action Issued in U.S. Appl. No. 14/410,536.
May 12, 2017 Office Action dated U.S. Appl. No. 14/410,536.

* cited by examiner

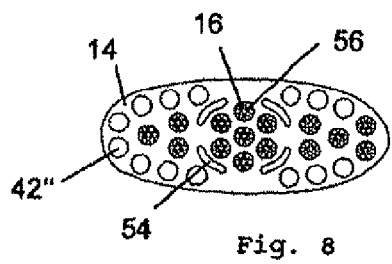
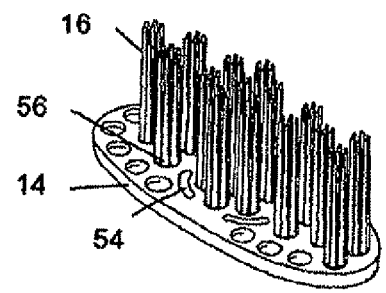
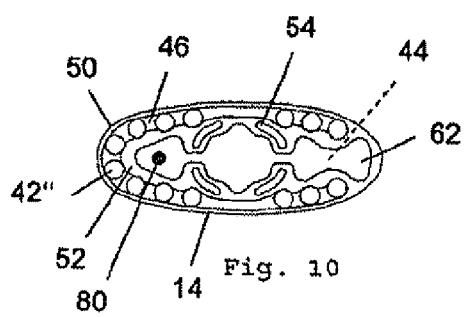
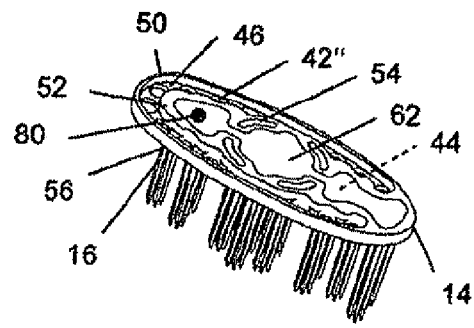
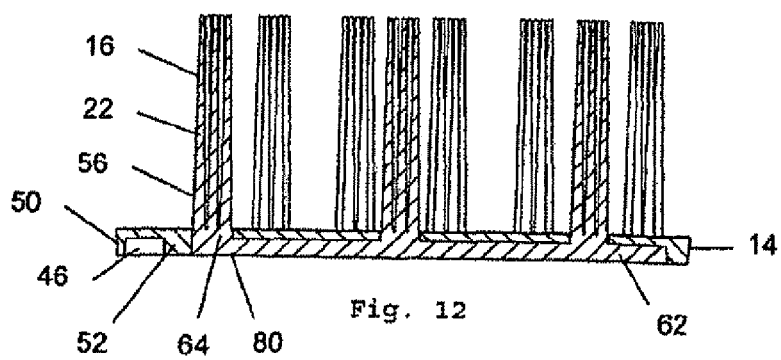
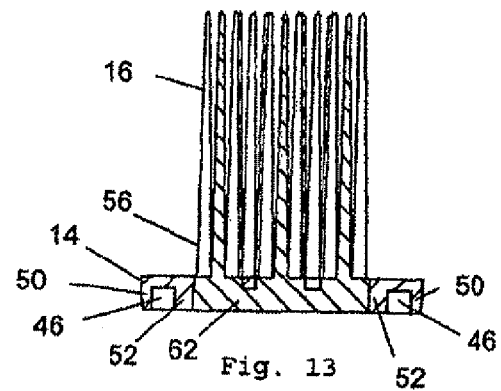

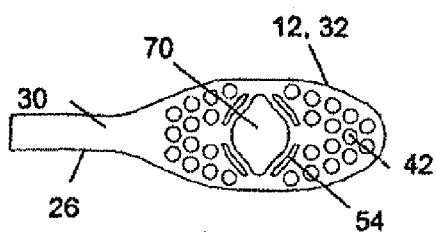
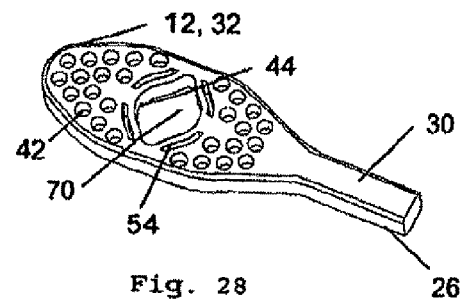
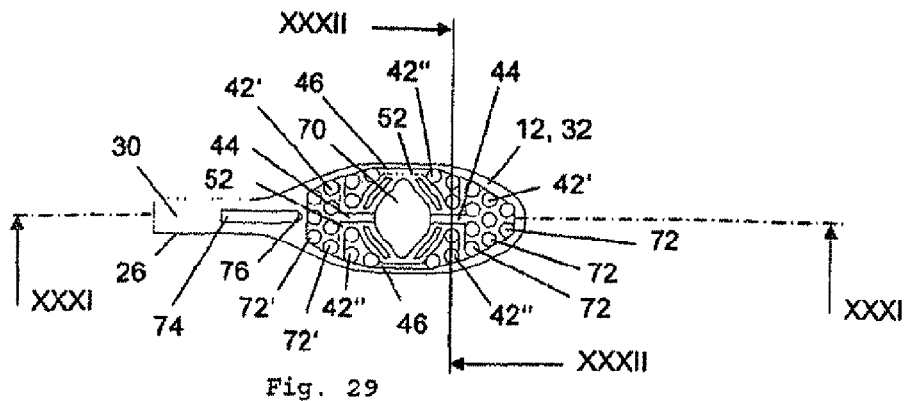
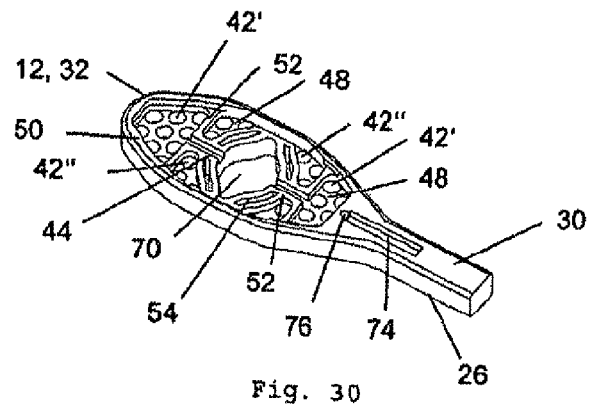
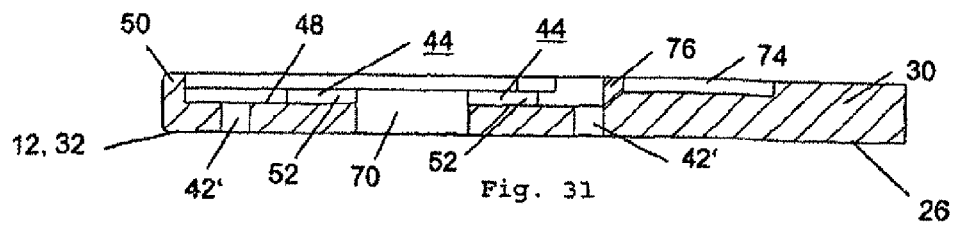
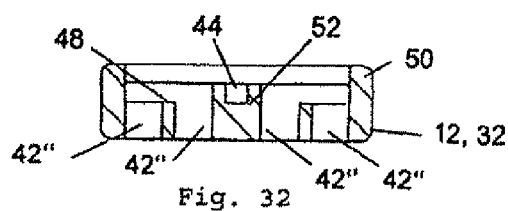

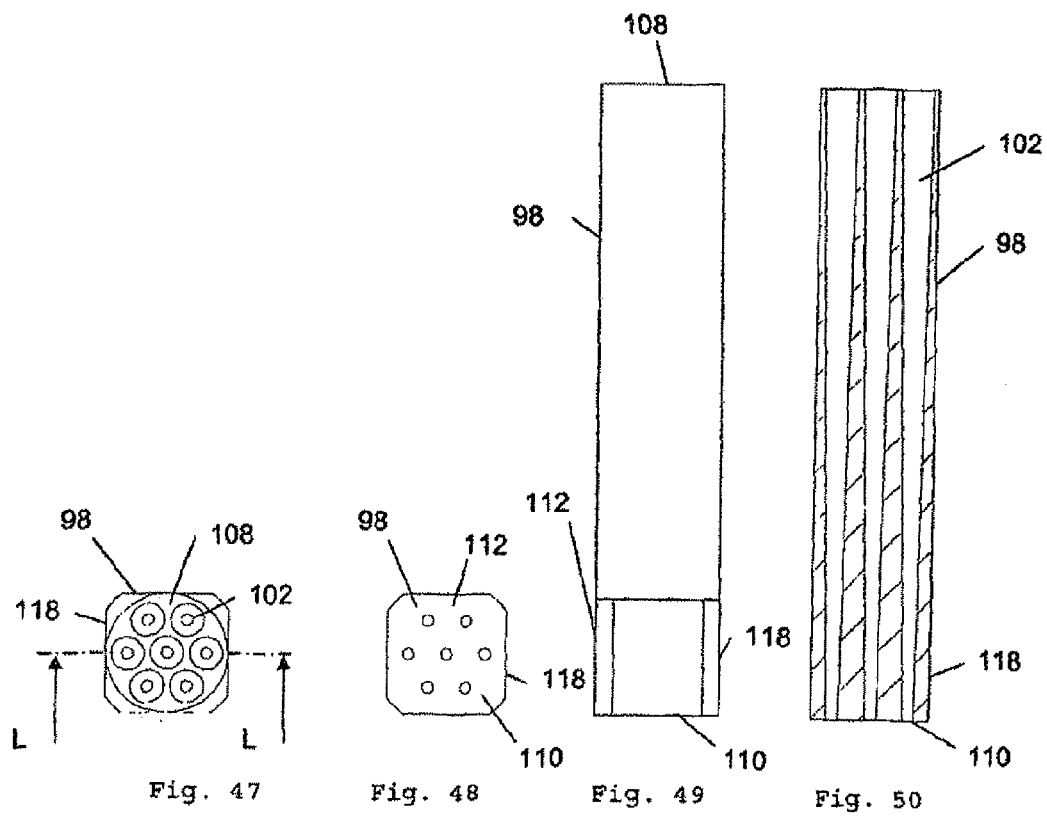
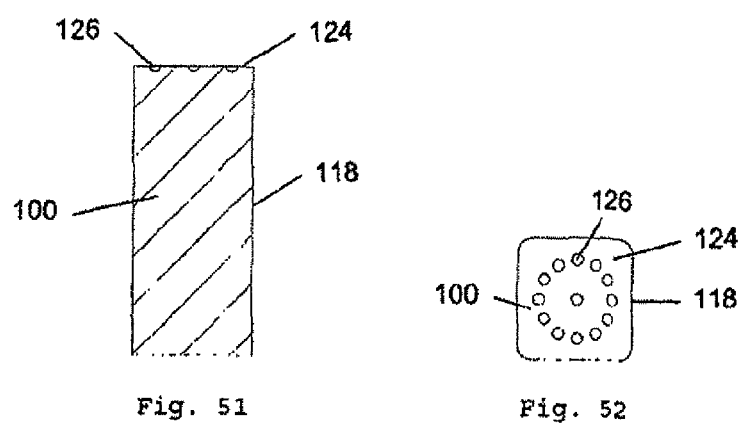

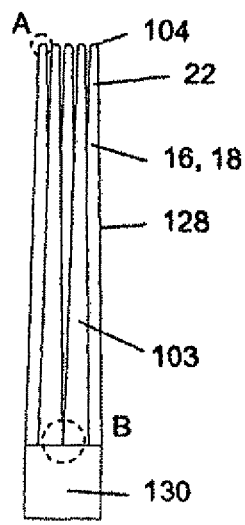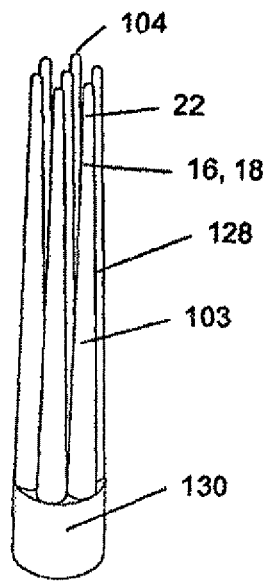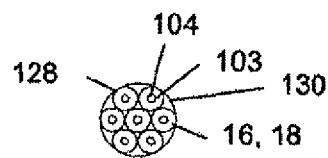
Fig. 55
Fig. 55a
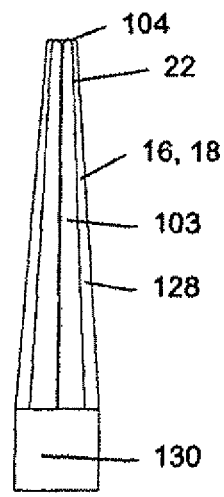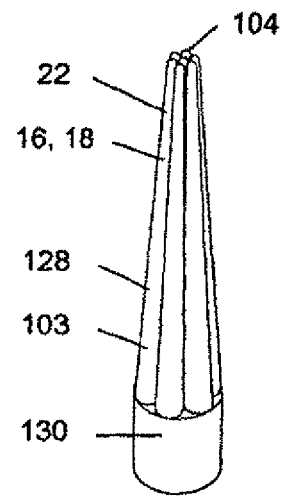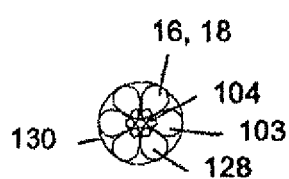
Fig. 56
Fig. 56a

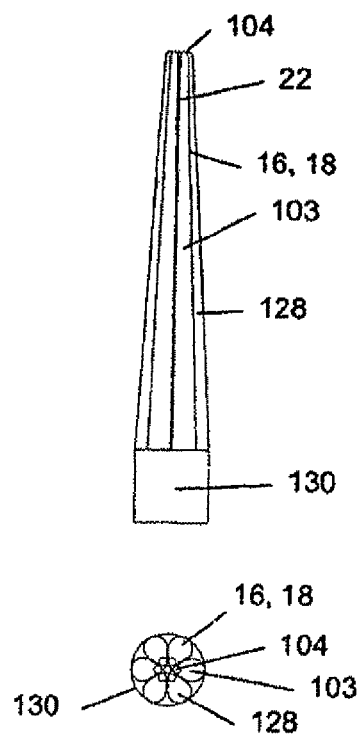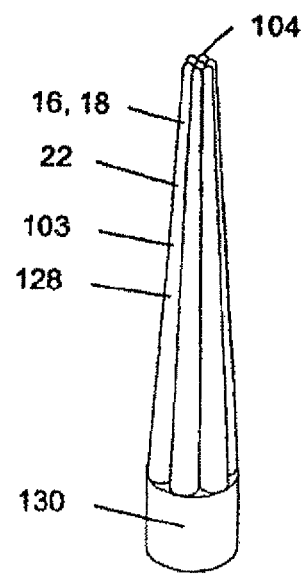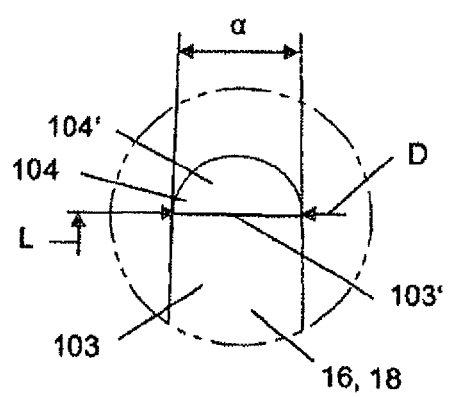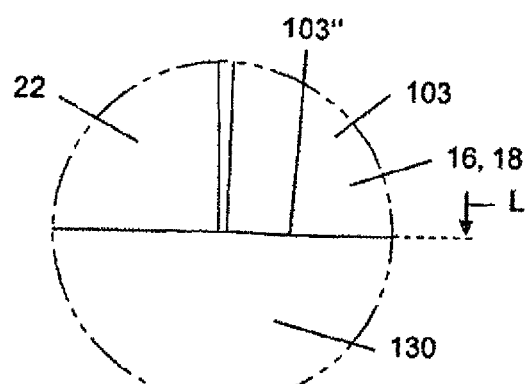
Fig. 57
Fig. 57a
Fig. 65
Fig. 66

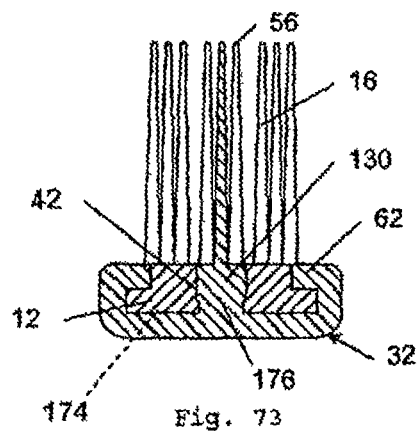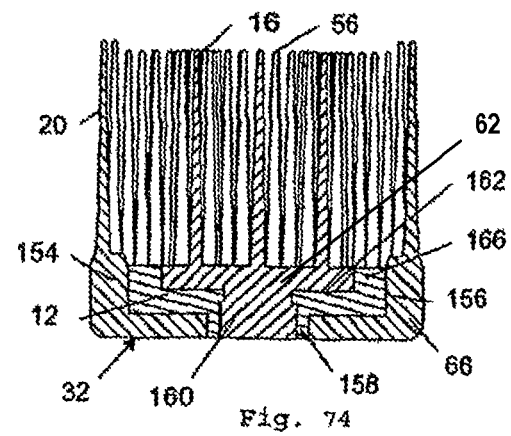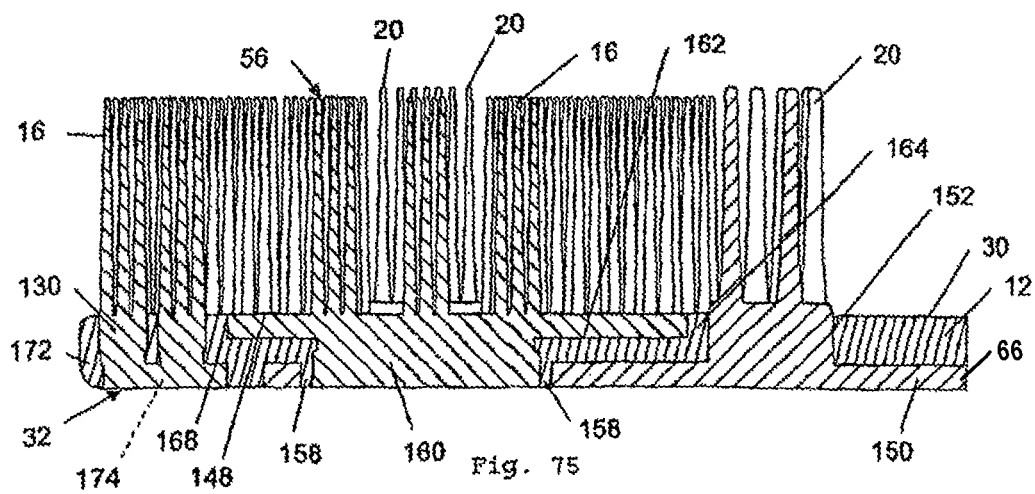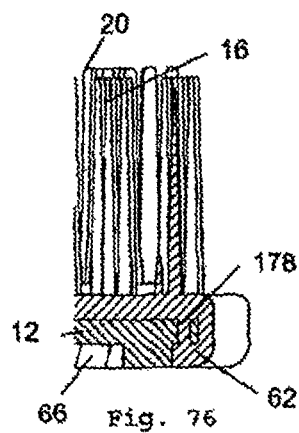

TOOTHBRUSH WITH INJECTION-MOULDED BRISTLES AND METHOD AND APPARATUS FOR PRODUCING THE SAME

BACKGROUND

Technical Field

The present invention relates to a toothbrush, to a method for producing a toothbrush of this kind and to an apparatus for producing a toothbrush.

Description of Related Art

Document WO 2008/135953 A1 makes known an oral hygiene implement, the head part of which has a base and a plurality of elastomer elements which protrude from the base. The elastomer elements can be produced using the injection molding method, the elastomer elements forming at least 250 edges and the tip radius of the elastomer elements being less than 0.006 inches.

In addition, document WO 03/079849 A1 discloses bristles for a bristle product, in particular a cleaning brush, a toothbrush or an application brush, the bristle having a lower root region by way of which it can be attached in or on a bristle carrier or is part of a bristle carrier and having a free length which is arranged outside the bristle carrier and is located above the root region. This is composed of a shaft region which adjoins the root region and a flex region which is arranged on top of said shaft region, the shaft region being composed of a lower shaft base portion which adjoins the root region and a shaft portion which lies above said shaft base portion. The flex region is composed of a lower acting and flex portion which adjoins the shaft region and a tip portion which lies above the acting and flex portion and forms the free end of the bristles. In the shaft base portion, the bristle has a continuous, recess-free lateral surface and in the flex region, at least in portions on the lateral surface, carries a profiling, which is formed by elevations and/or recesses and lies inside the enveloping surface of the bristle. The injection molding tool for producing said bristle consists of several mold plates which are layered transversely with respect to the longitudinal extension of the mold channel, each of which has a longitudinal section of the mold channel.

SUMMARY

It is an object of the present invention to create a simply producible toothbrush with injection-molded bristles and a method as well as an apparatus for producing a toothbrush of this type.

Said object is achieved with a toothbrush, a method and an apparatus as described below.

The further development of the toothbrush as claimed in the invention includes, along with the injection-molded bristles, further cleaning elements, in particular also inserted, previously extruded, conventional bristles and/or injection-molded (not with bristles) flexible massaging and cleaning elements.

The disclosure in conjunction with individual embodiments of the toothbrush as claimed in the invention and production methods with reference to injection-molded bristles, extruded conventional bristles and (bristle-free) injection-molded flexible massaging and cleaning elements are applicable in principle to all the embodiments, in particular to those according to FIGS. 1-25, 27-44, 58-60, 61-63 and 70-76.

A toothbrush as claimed in the invention has a bristle carrier, which is produced using the injection molding method and is provided with at least one distributing channel for bristle material. The injection-molded bristles, which are also produced using the injection molding method and have a bristle stem, protrude from the bristle carrier and are realized integrally, i.e. in one piece, with the bristle material in the distributing channel.

The injection-molded bristles are connected to the bristle carrier by means of material bonding and/or positive locking. The distributing channel serves for supplying the bristle material for the injection-molded bristles from an injection point. The injection point is provided in the injection molding tool by an injection nozzle and can usually be fixed on the toothbrush.

The toothbrush as claimed in the invention can be produced in a simple manner using the injection molding method, preferably using the one-component, two-component or multiple-component injection molding method.

The injection-molded bristles preferably have a conical form with a constant gradient (conical form) in the region of the bristle stem. A usage-side end region of the bristles, which is realized integrally with the bristle stem, preferably connects to the usage-side end of the bristle stem.

Said end region is specially formed and preferably has a substantially spherical form, a bristle cap. In particular, it can be realized in a hemispherical manner, in a cone-shaped manner or flatly with a rounded transition to the lateral surface of the bristle stem. It is also possible for it to be divided into a number of tapered end bristles.

The form of the usage-side end region is different to that of the bristle stem.

It is possible to dispense with a specially formed usage-side end region, the usage-side end of the injection-molded bristles being formed by a flat termination of the bristle stem with a sharp-edged transition to the lateral surface of the bristle stem.

As an alternative to this, the injection-molded bristles can also have different gradients or shoulders as long as it is ensured that they can be removed from the mold in the direction of the bristle carrier.

In the case of a preferred embodiment of the toothbrush, the ratio between the diameter of injection-molded bristles produced using the injection molding method at the usage-side end of the bristle stem and the (exposed) length of the bristle stem is at least 1:35. In a preferred manner, said ratio is at least 1:40.

In a further preferred embodiment of the toothbrush as claimed in the invention, the above-mentioned ratio is a maximum of 1:90, in a preferred manner a maximum of 1:80.

In a preferred manner the above-mentioned ratio lies between 1:35 and 1:90, preferably between 1:40 and 1:80.

The selection of said ratio also influences the bristle hardness (elasticity). The reduction of said ratio thus leads to harder elastic bristles. A toothbrush can have injection-molded bristles where such ratios are different.

The distributing channel for the bristle material of the injection-molded bristles can be situated on the front side of the bristle carrier facing the exposed length of the injection-molded bristles. In a preferred manner, however, it is realized on the rear side of the bristle carrier facing away from the exposed length of the injection-molded bristles. In this case, the bristle carrier has passages for the bristle material which extend from the bottom of the distributing channel to the front side.

In a particularly preferred embodiment, one passage of the bristle carrier has associated therewith several injection-molded bristles, in particular between 2 and 15, preferably between 3 and 10 bristles form one bristle bundle which is associated with one passage.

In a particularly preferred manner, 4, 5, 6, 7, 8 or 9 bristles are associated with one bristle bundle. The named number of injection-molded bristles is preferably combined on one circular passage to form one bristle bundle. However, bundle sizes which are independent of the passages can also be formed.

The individual bristle bundles with injection-molded bristles are spaced apart by a minimum spacing. In this case, it has been shown that a minimum spacing of less than 2 mm, preferably a spacing of between 0.1 and 1.5 mm allows for an optimum cleaning action with excellent interdental penetration of the injection-molded bristles.

Preferably, between 20 and 50 bristle bundles are present on a toothbrush head. In a particularly preferred manner, between 25 and 45 bundles with injection-molded bristles are provided.

A toothbrush as claimed in the invention with injection-molded bristles includes between 100 and 500 injection-molded bristles for a good cleaning action. Preferably, there are between 150 and 300 injection-molded bristles.

The injection-molded bristles combined to form a bristle bundle preferably all converge slightly toward their usage-side end, i.e. the longitudinal center axes of the individual injection-molded bristles have a slight inclination toward the longitudinal center axis of their bristle bundle, apart from one centrally arranged bristle at most. Said "moving closer together" of the ends of the injection-molded bristles influences the interdental cleaning in a very positive manner.

In the case of the embodiment of the toothbrush, where the distributing channel is realized on the rear side of the bristle carrier, the injection point for the bristle material, in a preferred manner, is offset with reference to the passages—also in a preferred manner in the longitudinal direction of the toothbrush—i.e. the injection point is not situated directly opposite a passage.

In an even more preferred manner, the injection point is positioned in the vicinity of the edge of the bristle carrier, outside the zone with the passages.

The injection point, in a preferred manner, is designed such that the material, after exiting from the nozzle, initially contacts the plastics material of the bristle carrier or of a small carrier plate forming the bristle carrier and does not directly contact a passage. As a result, an even distribution of the bristle material in the cavity is achieved and more even pressure conditions in the bristle cavities (compared over all the bristle cavities) are created.

The cross section (width and depth) of the distributing channels is dependent on the number of passages, the spacing between the passages and the injection point or on the maximum spacing of a passage from the injection point and on the bristle material.

In a preferred embodiment of the toothbrush as claimed in the invention, the height of the distributing channel—measured from its bottom as far as up to the surface forming the rear side or front side of the bristle carrier—is at least 0.5 mm. Said height is preferably between 0.5 and 2 mm, in particular between 0.7 and 1.5 mm.

The cross section of the distributing channel preferably corresponds to at least 35% of the cross section of the largest passage for the bristle material. In a further preferred manner, the cross section of the distributing channel corresponds to at least the area of the bristle bundle, a bristle base.

In a preferred further development, at least one bristle-free flexible massaging and cleaning element is injected on the bristle carrier. It protrudes on the same side of the bristle carrier as the injection-molded bristles. There can also be a bristle-free, flexible tongue cleaning element present. This latter is situated in a preferred manner on the side facing away from the bristles.

"Bristle-free" means that the flexible massaging and cleaning element or tongue cleaning element does not have any injection-molded bristles nor any extruded, conventional bristles.

The material for the bristle-free, flexible massaging and cleaning element (there can be several of them) can be distributed either by means of soft material distributing channels or in another manner. For example, a flat covering made of the material for the bristle-free, flexible massaging and cleaning element can be injected by means of the distributing channels which contain bristle material for the injection-molded bristles.

Thermoplastic polyurethane elastomers (TPE-U), thermoplastic styrene elastomers (TPE-S), such as, for example, a styrene-ethylene-butylene-styrene copolymer (SEBS) or a styrene-butadiene-styrene copolymer (SBS), thermoplastic polyamide elastomers (TPE-A), thermoplastic polyolefin elastomers (TPE-O) and thermoplastic polyester elastomers (TPE-E) are suitable as soft material for these types of bristle-free, flexible massaging and cleaning elements and for bristle-free tongue cleaning elements. In addition, thermoplastic polyethylene (PE) and polyurethane (PU) can be used as soft material; they can also be used as hard material. TPE-S is used in a preferred manner. The Shore A hardnesses of the soft materials are preferably less than 90 Shore A.

The Shore hardness of the soft material for the bristle-free, flexible massaging and cleaning element or elements is lower, in a preferred manner considerably lower than the Shore hardness of the bristle material for the injection-molded bristles.

The soft material for the bristle-free, flexible massaging and cleaning elements preferably has a Shore A hardness of less than 40.

If soft material is used in a handle part or neck part of a brush body of the toothbrush, it preferably has a Shore A hardness of less than 70 there. In general, when viewed over the entire toothbrush, the Shore A hardness of the soft materials is less than 90.

Bristle-free, flexible massaging and cleaning elements can be in different forms. For example, these can be in a stem-shaped almost cylindrical, sail-like, wavy, spherical, conical, crescent-shaped, star-shaped or cup-shaped form.

Bristle-free, flexible massaging and cleaning elements are preferably shorter than injection-molded bristles; this means that they do not project as far beyond the bristle carrier as injection-molded bristles.

Bristle-free, flexible massaging and cleaning elements are typically considerably more voluminous than injection-molded bristles. For this reason, materials with a lower Shore hardness can also be used for bristle-free, flexible massaging and cleaning elements. The long, thin development gives the injection-molded bristles their flexibility.

The bristle carrier can have one, two or even more distributing channels for bristle material. In this case, it is possible that a different bristle material is used per distributing channel for bristle material. The bristle material can differ in the color, the Shore hardness and/or other characteristics which are generated by means of adding elements (antibacterial, surface changing, etc.) to the master batch.

In addition, the bristle carrier can have one (or several) soft material distributing channel(s) for the soft material for the flexible massaging and cleaning elements. If two or more soft material distributing channels are present, it is possible for a different material to be used per soft material distributing channel. The soft material for bristle-free, flexible massaging and cleaning elements can also differ in the color, the Shore hardness and/or other characteristics which are generated by means of adding elements (antibacterial, surface changing, etc.) to the master batch.

In a further preferred embodiment of the toothbrush as claimed in the invention, in the bristle carrier the soft material distributing channel is separated from the distributing channel for the bristle material. Consequently, in said embodiment there is no contact between the bristle material and the soft material.

The distributing channels for the different materials are preferably separated by the hard material of the bristle carrier. This means that, using the injection molding method, in a simple manner it is possible, by means of one single injection point for the soft material, simultaneously to produce, on the one hand, injection-molded bristles from bristle material and, on the other hand, a bristle-free, flexible massaging and cleaning element, where applicable together with a bristle-free tongue cleaning element. The bristle-free, flexible massaging and cleaning element—or several of them—and, where applicable, the bristle-free tongue cleaning element, are realized integrally, i.e. continuously, with the soft material in the soft material distributing channel.

In a particularly preferred embodiment of the toothbrush as claimed in the invention, the bristle carrier has a small carrier plate produced using the injection molding method (FIGS. 1-25). The described characteristics for the bristle carrier are consequently also applicable in each case to the small carrier plate and vice versa. The distributing channel for the bristle material is realized on said small carrier plate as are, where applicable, the passages and the soft material distributing channel. The small carrier plate carrying the injection-molded bristles produced from the bristle material and, where applicable, the bristle-free, flexible massaging and cleaning elements is fastened on a brush body.

In a preferred manner, in a head region the brush body has a small carrier plate accommodating recess into which the assembled small carrier plate is inserted.

In a preferred manner, the small carrier plate on the brush body is fastened by means of ultrasound welding. Other types of fastening, however, are also possible such as bonding, snapping-in, latching or injecting around using the injection molding method. In the case of the latter, the small carrier plate with the injection-molded bristles and, where applicable, with the bristle-free, flexible massaging and cleaning elements, can be inserted once again into an injection molding tool; the connection can be formed by means of injecting over the brush body and the small carrier plate using a one-component, two-component or multiple-component injection molding method.

It is also possible to inject over the small carrier plate with the injection-molded bristles and, where applicable, with the bristle-free, flexible massaging and cleaning elements, once again inserted into the injection molding tool, and at the same time to form the brush body.

In the case of said two development variants, the small carrier plate can also be inserted into the injection molding tool only with the injection-molded bristles. Additional bristle-free, flexible massaging and cleaning elements or bristle-free tongue cleaning elements made of soft material can then be formed during the injecting-over process.

In other words, in these cases material zones made of soft material can be formed on the brush handle with the same soft material as the bristle-free, flexible massaging and cleaning elements or tongue cleaning elements. In this case, continuous material zones from one single injection point or non-continuous material zones from several injection points can be used.

The brush as claimed in the invention is a toothbrush, for example a manual toothbrush or an electric toothbrush. In the last-mentioned case, it is possible for the part realized as claimed in the invention to be a slip-on part/interchangeable part. The bristle carrier, which in this case is mounted so as to be movable, can be used, among other things, with electric toothbrushes with oscillating, pivoting or translatory movement, for vibratory or sonic toothbrushes or for electric toothbrushes with combined movements.

As a result of the serious wear and the high level of interdental action of the injection-molded bristles, said bristles can be used on electric toothbrushes at high movement frequencies. Injection-molded bristles are particularly suitable for movement frequencies of the bristle carrier of between 6,000 and 20,000, in a particularly preferred manner of between 12,000 and 18,000 pivoting movements per minute and between 8,000 and 12,000 oscillating movements per minute.

In order to minimize the potential of injury to the gums, attempts are made to obtain a path covered by the usage-side ends of the injection-molded bristles of less than 5 mm per direction, preferably a path of between 0.5 and 4 mm per direction.

The toothbrush as claimed in the invention can be designed both as a brush for a single use (disposable brush) and as a brush for multiple use (reusable brush analogous to common toothbrushes). In addition, bristle carriers or small carrier plates as claimed in the invention can be provided on the rear side or can be provided by means of a cavity also with a geometry for an exchangeable head system on toothbrushes and thus can serve as interchangeable heads for manual or electric toothbrushes.

The toothbrush as claimed in the invention can also be integrated in a tongue cleaner. The tongue cleaner, in this case, is provided with injection-molded bristles which treat the surface of the tongue. It is also possible to develop a tongue cleaner on the rear side of toothbrushes with injection-molded bristles as claimed in the invention.

When adapted, brushes as claimed in the invention can also be designed for interdental applications, as interdental brushes.

In place of a toothbrush, the brush as claimed in the invention can also be a brush for personal hygiene, in particular for cosmetics, for example for a mascara brush, a nail varnish brush, a hair brush or a hair-tint application instrument.

In addition, it is possible for the brush as claimed in the invention to be a domestic brush, in particular a washing-up brush or a floor wiper. Brushes as claimed in the invention are also conceivable as applicators in the area of medicine.

Although, in principle, it is also possible to produce the bristle carrier itself from the bristle material, it is, however, preferred for the materials of the bristle carrier and the bristle material to be different. In a preferred manner, the bristle carrier consists of a hard material. However, it is also possible for it to have a soft material in addition to the hard material, for example in order to achieve a particularly high level of flexibility of the bristle carrier at desired positions.

In the case of a small carrier plate, it is sensible for the hard material of the small carrier plate and the hard material of the brush handle to be identical or at least affine. As a result, it is ensured that when connecting the brush head to the small carrier plate by means of welding or over-spraying, a material bond is generated.

Several identical or different bristle carriers can obviously also be used on the toothbrush at least with injection-molded bristles. This makes sense in particular when the bristle carrier has several small carrier plates.

In addition, it is possible to develop the bristle carrier in a non-flat manner. The bristle carrier is preferably flat, however it is also possible to provide said bristle carrier with elevations, for example in order to develop injection-molded bristles or bristle-free, flexible massaging and cleaning elements with different exposed lengths.

In addition, it is possible not to connect the bristle carrier or the small carrier plate to the brush body or the head part of the brush body over its entire circumferential length nor to support it. For example, the bristle carrier or the small carrier plate can be connected to the brush body and supported only in the rear and front part in order, in this manner, to achieve greater flexibility of the bristle carrier or of the small carrier plate.

In a preferred manner, the bristle material is provided by polyimide elastomers, in particular Grillflex ELG5930 of Ems-Chemie AG (Grillflex is a trademark of Ems-Chemie AG) or polyester elastomers, in particular Hytrel 7248 of DuPont, Riteflex 655, Riteflex 663, Riteflex 672 RF Nat, Riteflex 677 of Ticona Polymers or Riteflex RKX 193 RF Nat of Ticona Polymers (Riteflex and Hytrel are trademarks of DuPont or Ticona Polymers). In a preferred manner, the bristle material for the injection-molded bristles has a hardness of between 10 and 100, preferably of between 30 and 80 Shore D, in a particularly preferred manner of between 50 and 80 Shore D.

Bristle materials up to 120 Rockwell D can be used in particular for hard bristles. The following hard materials, which are preferably used for the brush body and the bristle carrier or the small carrier plate, can also be considered for this purpose.

As hard material for the brush body and the bristle carrier or the small carrier plate, the following thermoplastics are particularly suitable:
  styrene polymers such as styrene acrylonitrile (SAN), polystyrene (PS), acrylonitrile butadiene styrene (ABS), styrene methyl methacrylates (SMMA) or styrene butadiene (SB);
  polyolefins such as polypropylene (PP) or polyethylene (PE) for example also in the forms of high density polyethylene (HDPE) or low density polyethylene (LDPE);
  polyesters such as polyethylene terephthalate (PET) in the form of acid-modified polyethylene terephthalate (PETA) or glycol-modified polyethylene terephthalate (PETG), polybutylene terephthalate (PBT), acid-modified polycyclohexylene dimethylene terephthalate (PCT-A) or glycol-modified polycyclohexylenedimethylene terephthalate (PCT-G);
  cellulose derivatives such as cellulose acetate (CA), cellulose acetobutyrate (CAB), cellulose propionate (CP), cellulose acetate phthalate (CAP) or cellulose butyrate (CB);
  polyamides (PA) such as PA 6.6, PA 6.10 or PA 6.12;
  polymethyl methacrylate (PMMA);
  polycarbonate (PC);
  polyoxymethylene (POM);
  polyvinyl chloride (PVC);
  polyurethane (PUR).

Quite especially suitable as hard material for the brush body and the bristle carrier or the small carrier plate is polypropylene (PP) with an E-modulus of between 1000 and 2400 N/mm$^2$, preferably of between 1300 and 1800 N/mm$^2$. A further very preferred hard material is polybutyl terephthalate (PBT), other materials also being possible. The choice of material is made in dependence on the required strength of the channel walls and of the bottoms of the distributing channels and, where applicable, of the soft material distributing channels of the bristle carrier or of the small carrier plate.

During the production of the bristle carrier or of the small carrier plate and of the brush body, the hard material and the soft material preferably form a material bond; identical or affine materials are used for this purpose.

Depending on the material combination, a material bond can also take place between the bristle materials and the hard materials/soft materials. However, if the materials are not affine, this means no material bond is formed, the materials can then be connected together (mechanically), for example, by means of friction locking or positive locking. In this case, the shrinkage of the bristle material in the distributing channels can generate friction locking and positive locking, which ensures reliable fastening of the bristle material on the bristle carrier or smaller carrier plate even without a material bond.

The positive locking can be optimized, for example, by the development of the channel walls. Said walls can have undercuts (which can result in forced removal from the mold) and in this way can form a geometry which enables improved positive locking of the bristle carrier or the small carrier plate with the material of the injection-molded bristles.

In addition, the positive locking can be improved as a result of the passage being somewhat widened (for example in a stepped manner) or opened conically in the direction toward the front side of the bristle carrier. The achievement here is that the small carrier plate is quasi clasped.

By means of over-spraying the distributing channel containing the bristle material with a soft or hard material, said distributing channel can also be encapsulated. In this case, the material to be over-sprayed preferably enters into a material bond with the bristle carrier or the small carrier plate. In this case, it is also possible to provide the soft material only on the rear side of the bristle carrier. The soft material, in this case, can be realized, for example, on both sides as far as into the side faces of the bristle carrier.

The channel walls of the distributing channels can be realized at different heights inside a small carrier plate or bristle carrier. In this case, it is also possible for a distributing channel for bristle material not to be realized until one or several bristle materials have already been injected in previous steps. This would mean that the channel walls are formed by the material of the bristle carrier or of the small carrier plate and the bottom of the distributing channel consists of bristle material and, for example, lower channel walls.

Channel walls can, in principle, protrude at different heights and can be covered at least in part with further materials (for example bristle material, soft material).

A further design provides that the toothbrush has a bristle carrier which is produced using the injection molding method and a surface layer made of bristle material which is injected onto said bristle carrier using the injection molding method. A plurality of injection-molded bristles is realized integrally with the surface layer using the injection molding method.

The bristle carrier consequently carries said injection-molded bristles indirectly by means of the surface layer.

It is conceivable for all the injection-molded bristles to protrude from the surface layer.

However, it is also possible for the plurality of injection-molded bristles to protrude from the surface layer and the remaining injection-molded bristles to be realized integrally with the bristle material in a distributing channel (or several distributing channels), as described further above.

In a preferred manner, in each case a number of the injection-molded bristles protruding from the surface layer form a bristle bundle.

In each case between 2 and 15 of said injection-molded bristles, in a preferred manner between 3 and 10, form a bristle bundle.

In a particularly preferred manner, in each case between 4 and 9 of said injection-molded bristles form a bristle bundle.

In a preferred manner, between 10 and 40, in particular between 15 and 30, bristle bundles are realized integrally with the surface layer and protrude from said surface layer.

The further embodiment consequently provides that the material distribution in the head part is not effected exclusively by means of channels, but can also be flat. In this case, once again, bristle material is inserted in the head part of the manual toothbrush, for example by means of an injection point in the handle part of the manual toothbrush and a supply channel to the head part or directly by means of an injection point in the head part. Once the bristle material has reached the head part, it is distributed in a flat manner and realizes the bristles.

In this case, in a preferred manner the bristle material is not guided through the bristle carrier or the small carrier plate for all the bristle bundles before it forms the bristles, but a part of the surface between the bristle bundles is also formed with the bristle material at the same time. In the case of said development variant, individual bristle bundles made of injection-molded bristles are formed directly from the surface of the bristle carrier, which is formed from bristle material, and protrude from said bristle carrier.

The bristle material is preferably distributed such that it enters into positive locking with the material of the brush body. The positive locking can take place in different ways, for example as a result of the brush body being penetrated and the bristle material, prior to and after the penetration, being spread out in a wider manner than the penetration, or of the brush body being wrapped around from the outside or through openings. When the materials are affine, the bristle material and the material of the brush body can realize a material bond.

The positive locking between the materials results in the bristle material taking up portions on different surfaces of the manual toothbrush. On account of the injection-molded bristles, the front side of the bristle carrier or small carrier plate is provided at least in part with bristle material.

Depending on the positive locking development, the bristle material is also applied on the side faces of the head part or on the rear side of the head part.

In addition, the injection-molded bristles of the previously mentioned embodiment can be combined with injection-molded bristles which are filled at least in part through distributing channels and push through openings in which, in each case, only one bristle bundle is anchored.

In addition, bristle-free, flexible massaging and cleaning elements can be mounted in the previously mentioned embodiment, for example, in or around the bristle field. Said elements are formed by a soft material. Said soft material can cover certain positions of the bristle material or can be completely separated from said bristle material.

In addition, conventional, extruded bristles as claimed in the disclosed development variants can also be used in the case of said development variant in the bristle carrier or in the small carrier plate.

In the case of the method for producing a toothbrush as claimed in the invention, a bristle carrier, or a small carrier plate, is produced using the injection molding method and at the same time at least the one distributing channel for the bristle material is realized. In addition, also using the injection molding method, the injection-molded bristles, which have a bristle stem, are realized integrally with the bristle material in the distributing channel.

In a particularly preferred manner, the bristle material is injected into the distributing channel. One bristle material can be distributed per distributing channel.

In a preferred manner, a small carrier plate with the distributing channel is produced as the bristle carrier using the injection molding method along with the injection-molded bristles. The two-component or multiple-component injection molding method is suitable, in particular, for this purpose. The small carrier plate provided with bristles in this manner is then fastened on a brush body, preferably by means of ultrasound welding or over-spraying with the hard components and/or soft components of the brush body.

In a preferred manner, the brush body is also produced using the injection molding method.

In a particularly preferred manner, for the production of the brush body, at least in the region which interacts with the small carrier plate, the same or an affine material is used as for the production of the small carrier plate in order to achieve a material bond for the connection by means of over-spraying or welding. However, it is also possible to use different materials.

A particularly simple production is produced when the brush body with the distributing channel is produced using the injection molding method and the bristle material is injected into the distributing channel of the brush body to produce the injection-molded bristles. The brush body, in this case, has at least one head part which carries the injection-molded bristles, consequently forming the bristle carrier. In a preferred manner, however, the brush body is also provided with a handle part which is realized integrally with the head part. In the case of a toothbrush, in a preferred manner the brush body has a neck part between the handle part and the head part.

The present invention consequently also relates to a toothbrush with a brush body, which is produced using the injection molding method and on which the distributing channel for the bristle material is integrally formed in the head part such that the brush body forms the bristle carrier.

The brush body itself can be produced using the two-component or multiple-component injection molding method. In this case, different hard materials or also hard and soft materials can be used in the known manner.

At this point it must be mentioned that the distributing channel for the bristle material can extend from the head part right into the neck part or handle part. The injection point for the bristle material does then not have to be situated in the head part but can be situated in the neck part or handle part.

The brush body can be provided with an injection channel, preferably outside the head part, said injection channel being connected to the distributing channel by means of an injection passage which preferably extends into the interior of the brush body.

In one production variant the production of the toothbrush can take place in a cubed tool. Four stations which make the forming and processing of the toothbrush possible are incorporated in the tool. In a first station the basic body, consisting of the brush body with the handle part, the neck part and the head part, is produced from hard material. A second station serves for cooling the basic body or also for further processing of the basic body, whilst subsequently in the third station, the further injection molding materials are applied to the basic body, for example materials for the forming of the injection-molded bristles from bristle material and/or of the bristle-free, flexible massaging and cleaning elements. The product is removed in the fourth station.

Rational production can be effected by the direct or indirect linking of the following processes with the injection molding process. In this case, the toothbrushes produced in the injection molding process are not removed from the production process but are processed further in a direct or indirect manner. The term indirect, in this case, does not refer to removal from the process, but, for example, to buffering.

The path of the toothbrush can be provided with different further processing processes from injection molding to packaging. Examples of such processing processes are embossing (identifying or decorating, providing with the batch number, etc.). However, buffer stations can also be incorporated in the process so that a certain decoupling of the process steps can be effected and the steps can include a certain independence.

Packaging is effected at the completion of the production chain. In this case, the product is wrapped by way of packaging. Examples of this are blister packaging, bag packaging, etc.

The apparatus for producing brushes as claimed in the invention, in particular toothbrushes, is also suitable for carrying out the method as claimed in the invention. Said apparatus has an injection molding tool with a carrier cavity which is determined for the purpose of accommodating a bristle carrier. In addition, the tool has a first and a second tool insert.

The first tool insert is provided with at least one continuous bristle cavity for realizing the bristle stem of the bristle. Said bristle cavity is fluidly connected to the carrier cavity, i.e. it connects thereto and allows a flow of material between the carrier cavity and the bristle cavity.

The second tool insert serves for realizing the usage-side end of the bristle stem or the usage-side end region of the injection-molded bristle, in particular the bristle cap. In the case of said alternative, the second tool insert has a cap cavity which is preferably closed and only open toward the bristle cavity.

Said embodiment of the injection molding tool enables the use of different steels which are particularly suitable in each case. In particular, the one-piece, separate realization of the first tool insert means that the bristle cavity can be produced very thinly in comparison to its length, for example by means of laser cutting and electric discharge wire cutting. In addition, it is possible to use a material for the second tool insert that is different from the first tool insert, in particular a more favorable or optimized material.

As is usual in injection molding tools, the first and the second tool insert for the bristle material abut against one another in a sealing manner. The extremely small gap, however, can serve for the ventilation of the bristle cavity and of the cap cavity. It is also possible to use porous tool inserts which allow the air to be able to escape through the tool insert.

As the bristle cavity and the cap cavity have a very small diameter, the first and the second tool insert have to be aligned on top of one another in a precise manner. In a preferred manner, this is achieved by means of a block, for example made of tool steel, which has a guide recess to accommodate both the first and the second tool insert. The alignment of said two tool inserts is effected, in particular, by means of a polygonal contour, in particular a four-edged contour.

In a preferred manner, the first tool insert is produced from a powder-metallurgical steel.

The production methods of powder-metallurgy are characterized by the mechanical compression of metal powders in molds or presses and the simultaneous or subsequent sintering of the "green compact" at high temperatures or hot-rolling to form a block. For example, the powder-metallurgical steel Microclean M390 of Böhler Edelstahl GmbH & Co. KG is suitable (Microclean is a trademark of Böhler Edelstahl GmbH & Co. KG). In a preferred manner, said special powder-metallurgical steel is selected on account of the very small dimensions of the start hole to be created by means of laser cutting for the wire eroding process. The minimized number of material inclusions, the grain sizes in the steel and the regular structural constitution are optimized in the case of said steels. As a result, it is possible for the very fine laser beam to be able to penetrate the material over the length which is very long compared to the diameter. Said process is very robust or reproducible because precisely said powder-metallurgical steel is used. In addition, the steel must also be hardened and rust-resistant.

The surfaces of the bristle cavities and cap cavities are preferably not surface-treated on account of the small dimensions, whereas the surface quality or the surface roughness is clearly predetermined so that, in conclusion, a robust injection molding process can be achieved where the bristles are simply removed from the mold and do not get caught. The $R_a$ value of the surface is within the range of between 0.06 and 0.12, preferably between 0.07 and 0.1. In the case of the predetermined demolding conical forms for the injection-molded bristles, $R_a$ values of 0.6 for example are no longer functional.

In a preferred manner, the first tool insert has several bristle cavities and the second tool insert has several cap cavities. In particular, the number of bristle cavities corresponds to the number of injection-molded bristles for a bristle bundle, as mentioned further above; the number of bristle cavities is equal to or greater than the number of injection-molded bristles for a bristle bundle.

The injection pressures applied in the injection molding method are within a high range. The injection pressure for the production of first and second type bristles is greater than 800 bar, preferably between 1200 bar and 2000 bar, but preferably lower than 2200 bar.

In a preferred manner, the diameter of the injection-molded bristles produced using the injection molding method is between 0.5 and 1 mm at the bristle-carrier-side end, in a preferred manner between 0.75 mm and 0.9 mm. The diameter of the bristle stem at its usage-side end is between 0.05 mm and 0.4 mm, preferably between 0.15 mm and 0.35 mm.

The diameter of the bristle stem preferably reduces continuously from its bristle-carrier-side end as far as up to its usage-side end. Consequently, the injection-molded bristles, apart from the specially formed usage-side end region of the injection-molded bristles, are conical in form.

In a preferred manner, the cross section of the injection-molded bristles is circular. However, it can also be elliptical, star-shaped or polygonal, in principle it can assume an arbitrary closed contour. Moreover, a change in the form over the length of the injection-molded bristles is possible. The possibilities for removal from the mold or for forced removal from the mold are the limitations in this respect.

The bristle cap or the specially formed usage-side end region of the injection-molded bristle itself can be conical, hemispherical or can have a rounded transition to the lateral surface of the bristle stem. Moreover, it is possible to divide up the free end region of the injection-molded bristles and thus to form an injection-molded bristle with several ends.

It is also possible to realize the free end of the injection-molded bristle by means of the flat end of the bristle stem with a sharp-edged transition to the lateral surface of the bristle stem.

The geometry of the injection-molded bristles is designed such that they are tapered over the length toward their free end. The ability to be removed from the mold is a factor to be taken into consideration; in addition, injection-molded bristles which are tapered toward their free end penetrate better into the spaces between the teeth. This is analogous to extruded, conventional tapered bristles.

In this way, the injection-molded bristle can obtain the form of a truncated cone or a pyramid, with the above-mentioned possibilities for the end region, the developed and specified cone forms being very small and hardly perceived by the consumer. However, developing greater cone forms which are also visible in the end cannot be excluded.

If small carrier plates are used as bristle carriers, their overall thickness is preferably between 0.7 mm and 2.0 mm, in particular between 1.2 mm and 1.6 mm.

The wall thickness of the small carrier plate in the region of the distributing channels, for example measured between the bottom of the distributing channel as far as up to the front side of the small carrier plate, is preferably between at least 0.3 mm and 1.2 mm, in particular between 0.7 mm and 1 mm.

Using an injection molding tool, it is also possible to produce so-called individual bundles of injection-molded bristles by means of the first and second tool insert.

The separate individual bundles have a bundle stem, from which a number of injection-molded bristles protrude, for example between 2 and 15, in particular between 3 and 10. In a preferred manner, the number of bristles specified in conjunction with the bristle bundles also applies to the individual bundles.

In a preferred manner, the exposed length of the bristles begins with its outlet from the bristle carrier such that, where there are passages in the bristle carrier, a bristle base in which the injection-molded bristles are connected integrally to one another, is formed in the region of the passages.

As an alternative to this, the bristle base can also be developed so as to protrude beyond the bristle carrier. This leads to the exposed length of the injection-molded bristles not beginning until at a spacing from the bristle carrier. Said spacing can be up to 5 mm. Consequently, it is also possible to adjust the hardness/elasticity of the injection-molded bristles.

In a preferred manner, the bristle base, and consequently the passages, have a diameter of between 1.5 mm and 3.5 mm, preferably between 1.9 mm and 2.6 mm. These same dimensions can also apply to the bundle stem.

As an alternative to this, several bristle bases can together form a common zone which is placed in one single passage. The advantage of said development variant is that the injection-molded bristles of said zone are suspended in a more flexible manner and the common bristle base is able to be deformed correspondingly in relation to the bristle carrier.

In a further development form several bristle bundles can also protrude from a flat zone, consisting of bristle material. The advantage of said development variant is that the injection-molded bristles do not require any passages through the hard material of the bristle carrier, or of the small carrier plate. It must be mentioned at this point that in addition to the injection-molded bristles produced using the injection molding method, the bristle carrier can also be provided with extruded, conventional bristles, for example using the AFT method (Anchor Free Tufting). In this case, as described above, the bristle carrier or the small carrier plate is provided in advance with injection-molded bristles and, where applicable, with bristle-free, flexible cleaning and massaging elements.

In this case, however, some (continuous) passages determined for the conventional bristles are left open. The extruded, conventional bristles are subsequently guided through said passages and are then melted on the rear side of the bristle carrier or of the small carrier plate on their ends facing away from the usage side. Consequently, a melt carpet, which adheres to the bristle carrier or small carrier plate, is formed for the fastening of the extruded, conventional bristles. Said melt carpet can cover, at least in part, the supply channels of the bristle material for the injection-molded bristles.

When the bristle carrier or small carrier plate is provided with extruded, conventional bristles by means of anchor punching, blind holes are realized in the bristle carrier or small carrier plate instead of the mentioned continuous passages, said blind holes being provided with the conventional bristles by means of anchor punching. As in the case of the AFT method, the bristle carrier or small carrier plate is provided beforehand with injection-molded bristles and, where applicable, with bristle-free, flexible cleaning and massaging elements.

In the case of in-mould methods (IAP or IMT), contrary to AFT or anchor punching, the extruded, conventional bristles are injected around in the injection molding tool with the hard and/or soft material of the bristle carrier on their ends facing away from the usage-side end for anchoring on the bristle carrier. The bristle carrier or small carrier plate, as described previously, is then provided with injection-molded bristles and, where applicable, flexible cleaning and massaging elements.

The extruded, conventional bristles can be developed in a cylindrical or tapered manner. Said bristles are preferably produced from polyamide (PA) or polyester (PET). The cylindrical part of said bristles has a diameter of between 0.1 and 0.3 mm, preferably between 0.15 and 0.225 mm. Said extruded, conventional bristles are also preferably used in further bristle bundles.

Approximately between 20 and 300 usage-side bristle ends are used per further bristle bundle with extruded, conventional bristles. The number of bristles of a further bristle bundle with extruded, conventional bristles is consequently considerably greater than the number of bristle ends of a bristle bundle with injection-molded bristles. The ratio between the numbers is between 1:2 and 1:40, preferably between 1:2 and 1:10.

Extruded, conventional bristles are advantageously longer than injection-molded bristles.

Advantageously, zones with bristle bundles of injection-molded bristles alternate with zones with further bristle bundles of extruded, conventional bristles. For example, said alternating rows can be in the longitudinal or transverse direction.

As an option, further bristle bundles, which do not stand at right angles with respect to the surface of the bristle carrier, can be formed of extruded, conventional bristles. For example, such further bristle bundles can form a so-called X position or can protrude laterally beyond the brush head. This can certainly also be done with injection-molded bristles, however is more expensive to produce.

In addition, zones with bristle bundles made of injection-molded bristles can be surrounded by bristle-free, flexible cleaning and massaging elements.

It is also possible not to inject the bristle-free, flexible massaging and cleaning elements on the bristle carrier, but to insert them into the bristle carrier so as to be movable or non-movable by means of frictional or positive locking, for example by means of a snap-type connection or a weld connection.

It must also be mentioned that water-soluble, injectable polymers can be used as bristle material, hard material and/or soft material. Active substances which are released when the brush is used in contact with water, in particular in the case of toothbrushes, can be included in said polymers. In addition, it is possible to develop elements with the water-soluble, injectable polymers which are then mounted in the head part of the toothbrush.

The exposed length of the injection-molded bristles is preferably between 4 mm and 16 mm, in particular between 8 mm and 12 mm, this is in particular in the case of toothbrushes.

In addition, the injection-molded bristles, in particular for problem-free removal from the mold, have a minimum cone angle of between 0.5° and 5°, in a preferred manner between 0.8° and 2°, in a particularly preferred manner between 0.8° and 1.5°.

Means, which support the process of removing the injection-molded elements from the mold, so-called mold removal aids, can be added to the bristle material and also to the soft material. Said means are preferably added to the granulate by means of the master batch.

In addition, it is also possible to treat the injection molding tool or the cavity thereof regularly with lubricant in order to improve removal from the mold.

The corresponding dimensions for the injection molding tool or the first and second tool inserts are also produced from the specified dimensions for the injection-molded bristles.

Separately produced individual bundles can also be fastened by inserting the bundle stem into corresponding recesses on the bristle carrier, or can be injected around with the material for the bristle carrier.

Further, less preferred development variants for brushes with injection-molded bristles of the named type vary for example in the number of injection-molded bristles per bristle bundle.

Thus, it is possible to form a bristle carpet in which 35 or more injection-molded bristles are incorporated. The bristles, in this connection, preferably abut one against the other. The disadvantage of using said bristle carpets on toothbrushes is that the interdental action of the toothbrush is impaired.

Surface bundles with between 13 and 35 injection-molded bristles, preferably between 16 and 28 injection-molded bristles, can be used in order to develop bristle bundles which are very similar to the brushes produced using the AFT method. The injection-molded bristles once again preferably abut against one another. The area of the injection-molded bristles is geometrically open.

In general it is such that a large variety of variants can be achieved through the design of a toothbrush with distributing channels and passages and the corresponding design of the injection molding tool. With one development of the bristle carrier or small carrier plate, it is possible to create diverse bristle field configurations. For, in a preferred manner, the individual first and second tool inserts are exchangeable in a simple manner. Other bristle forms or flexible massaging and cleaning elements can be generated rapidly on a bristle carrier or small carrier plate in this way; in a preferred manner the passages are positioned in the same location and they are the same size for this purpose. Thus, in one development, injection-molded bristles can be formed in the passages of a distributing channel and in the other development it can be flexible massaging and cleaning elements.

The small exchangeability additionally provides advantages with reference to the production or the error costs. The production of the first tool inserts or of the bristle cavities is technically very demanding. The smallest particles in the material from which the insert is to be created can result in an error in the process or in the operating result. Errors in the region of the bristle cavities lead to the corresponding cavities in many cases causing non-tolerable errors on the product.

The combination of a non-flat small carrier plate together with a pair of tool inserts (first and second tool insert) arranged at an angle enables the forming of bristle bundles which are at an angle to the direction of removal from the mold or to the direction of opening of the injection molding tool. Said tool inserts are either moved prior to the complete removal of the bristle field from the mold such that at the same time the injection-molded bristles are removed from the mold, or they are arranged at an angle which allows for a forced removal from the mold. In this way, it is possible to create bristle bundles with injection-molded bristles arranged in an X-shaped or V-shaped manner or bristle bundles arranged protruding laterally or bristle bundles with injection-molded bristles which do not protrude at right angles from the bristle field.

The application possibilities open up due to said possible variants; they are limited by the injection molding possibilities.

As an alternative to forced removal from the mold, the tool inserts for the injection-molded bristles can also be developed so as to be movable in order to achieve the inclined position of the bristle bundles.

The development of the toothbrush or the arrangement of the bristle bundles and of the bristle-free, flexible massaging and cleaning elements can be effected on the head part in a symmetrical or asymmetrical manner with reference to the longitudinal axis and the center cross axis of the bristle field.

Different boundary conditions exist for the arrangement of the bristle bundles. In a preferred manner, the distance between the edges of the bristle bundles is at least as much as the width of a channel wall. The distance between individual bristle bundles on the brush is provided as a result of the geometries in the injection molding tool and in a preferred manner is between 0.4 mm and 0.8 mm, preferably between 0.4 mm and 0.6 mm.

In the present context, the term "injection-molded bristles" refers to such which are produced from bristle material by means of injection molding during the production process of the toothbrush. The term "extruded, conventional bristles" refers to such which are produced separately from the production process of the toothbrush in a known manner using the extrusion method and then, in the production process of the toothbrush, are fastened on the bristle carrier by means of anchor punching or using the AFT or IMT method. "Flexible massaging and cleaning elements" and "tongue cleaners" are neither injection-molded bristles nor extruded, conventional bristles; they serve a purpose other than the named bristles.

The present invention is explained in more detail by way of exemplary embodiments shown in the drawing, in which, purely schematically:

BRIEF DESCRIPTION OF THE DRAWINGS

FIG. 8 shows a top view of the small carrier plate with first type injection-molded bristles;

FIG. 9 shows the small carrier plate in the identical representation as FIG. 3 with first type injection-molded bristles from FIG. 8;

FIG. 10 shows a bottom view of the small carrier plate from FIG. 8 provided with first type injection-molded bristles, with the relevant distributing channel filled with bristle material;

FIG. 11 shows the same view as FIG. 5 of the small carrier plate from FIG. 8 provided with first type injection-molded bristles;

FIG. 12 shows the same representation as FIG. 6 of the longitudinal section through the small carrier plate from FIG. 8 which is provided with first type injection-molded bristles;

FIG. 13 shows the same representation as FIG. 7 of the cross section of the small carrier plate from FIG. 8 which is provided with first type injection-molded bristles;

FIG. 27 shows a top view of the front side of a neck part and of a head part of a toothbrush body with passages for the bristle material and flexible material;

FIG. 28 shows a perspective inclined top view of the same part of the toothbrush body as in FIG. 27;

FIG. 29 shows a bottom view of the rear side of the same part of the toothbrush body as FIGS. 27 and 28;

FIG. 30 shows a perspective inclined bottom view of the same part of the toothbrush body as in FIGS. 27 to 29;

FIG. 31 shows a longitudinal section along the line XXXI-XXXI of FIG. 29 through the part of the toothbrush body shown in FIGS. 27 to 30;

FIG. 32 shows a cross section along the line XXXII-XXXII of FIG. 29 through the part of the brush body shown in FIGS. 27 to 31;

FIG. 47 shows a top view of a first tool insert for producing injection-molded bristles;

FIG. 48 shows a bottom view of the first tool insert;

FIG. 49 shows a projection of the first tool insert;

FIG. 50 shows a longitudinal section of the first tool insert along the line L-L of FIG. 47;

FIG. 51 shows a longitudinal section of a second tool insert along the line LI-LI of FIG. 52;

FIG. 52 shows a top view of the second tool insert;

FIG. 55 shows a projection and top view of a second embodiment of an individual bundle;

FIG. 55a shows a perspective top view of the second embodiment of the individual bundle;

FIG. 56 shows a projection and top view of the first embodiment of the individual bundle after cooling;

FIG. 56a shows a perspective top view of the first embodiment of the individual bundle after cooling;

FIG. 57 shows a projection and top view of the second embodiment of an individual bundle after cooling;

FIG. 57a shows a perspective top view of the second embodiment of the individual bundle after cooling;

FIG. 65 shows in an enlarged manner part of an injection-molded bristle identified in FIG. 55 by the reference A;

FIG. 66 shows in an enlarged manner part of two injection-molded bristles identified in FIG. 55 by the reference B;

FIG. 73 shows a first cross section along the line LXXIII-LXXIII through the toothbrush according to FIGS. 70-72;

FIG. 74 shows a second cross section along the line LXXIV-LXXIV through the toothbrush according to FIGS. 70-72;

FIG. 75 shows a central longitudinal section along the line LXXV-LXXV through the toothbrush according to FIGS. 70-72;

FIG. 76 shows a section along the line LXXVI through part of the head part of the toothbrush according to FIGS. 70-72;

DETAILED DESCRIPTION

Figure 1:
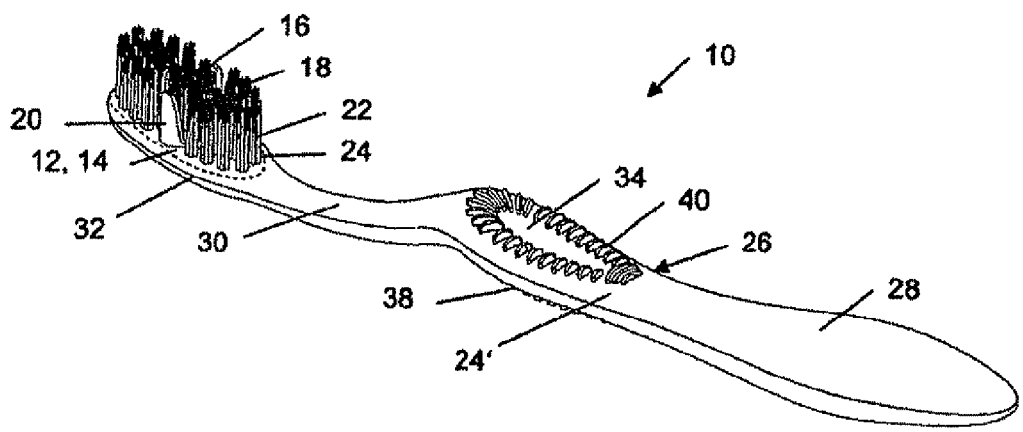
FIG. 1 shows a perspective view of a toothbrush as claimed in the invention with injection-molded bristles and flexible massaging and cleaning elements.
Figure 2:
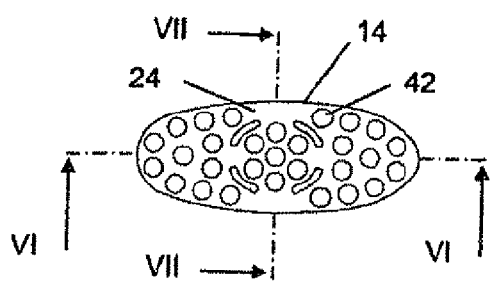
FIG. 2 shows a top view of a small carrier plate for injection-molded bristles and flexible massaging and cleaning elements for the toothbrush according to FIG. 1.
Figure 3:
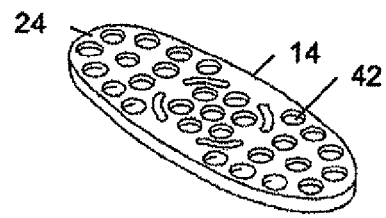
FIG. 3 shows a perspective inclined top view of the small carrier plate from FIG. 2.
Figure 4:
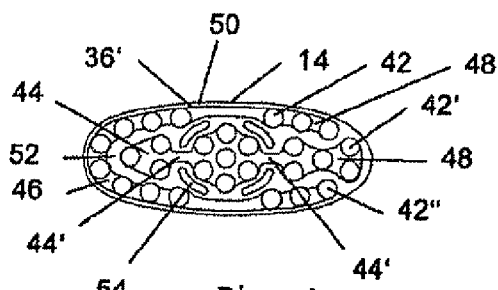
FIG. 4 shows a bottom view of the small carrier plate from FIG. 2.
Figure 5:
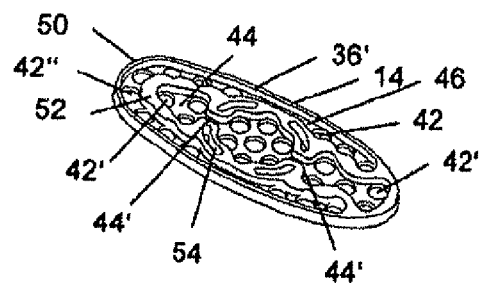
FIG. 5 shows an inclined bottom view in perspective of the small carrier plate from FIG. 2.

FIG. 1 shows a brush as claimed in the present invention realized as a manual toothbrush 10. As a bristle carrier 12, it has a small carrier plate 14, from which protrude first type injection-molded bristles 16, second type injection-molded bristles 18 and—bristle-free, i.e. not having bristles—flexible massaging and cleaning elements 20. Only the front side of the small carrier plate 14 facing the exposed part 22 of the injection-molded bristles 16, 18 and the exposed part of the flexible massaging and cleaning elements 20 can be seen in FIG. 1. The flexible massaging and cleaning elements 20 serve both for cleaning the teeth and for massaging the gum and the roof of the mouth.

The manual toothbrush 10 also has a brush body 26. In this case, said brush body consists of a handle part 28, a neck part 30 connecting integrally thereto and a head part 32 carried by the neck part 30. The head part is provided with a trough-shaped recess, not visible here, into which the small carrier plate 14, which is provided with the injection-molded bristles 16, 18 and the flexible massaging and cleaning elements 20, is inserted and is fastened preferably non-releasably on the head part 32. The fastening can be produced, for example, by means of ultrasound welding. To this end, the small carrier plate 14 preferably has a weld edge. However, as described further above, other suitable fastenings such as bonding, injecting around, shrinking-on and snap-type connections, etc. are also possible.

Figure 24:
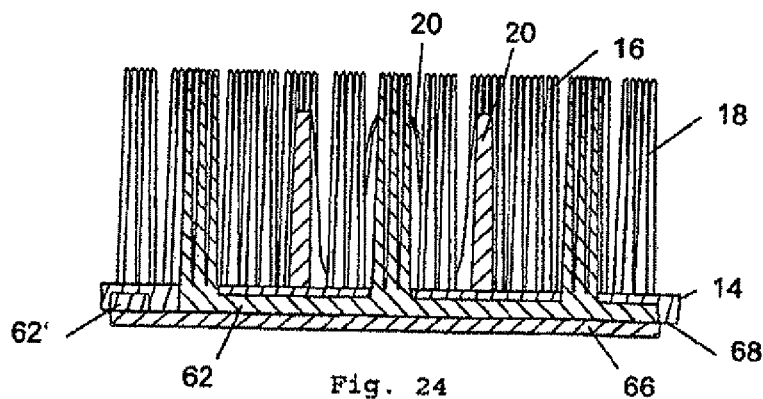
FIG. 24 shows the longitudinal section of the same representation as FIGS. 6, 12 and 18 of the small carrier plate from FIG. 20 with first and second type injection-molded bristles as well as the flexible massaging and cleaning elements.
Figure 25:
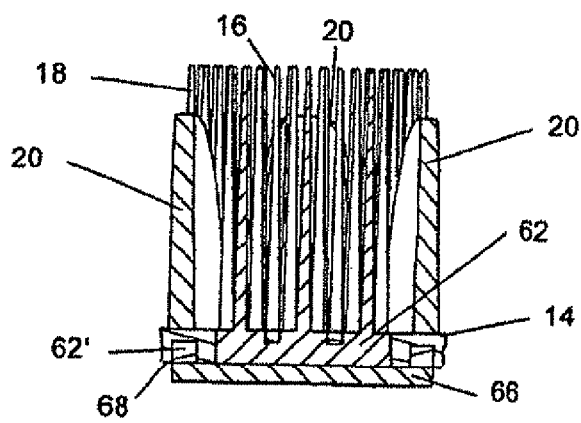
FIG. 25 shows the cross section of the same representation as FIGS. 7, 13 and 19 of the small carrier plate from FIG. 20 provided with first and second type injection-molded bristles as well as with flexible massaging and cleaning elements.

If the small carrier plate 14 is welded into a geometry in the head part 32, for the welding process recourse can be made, for example, to the known welding parameters and welding geometry from the AFT process (Anchor Free Tufting), i.e. the trough-shaped recess as also the corresponding geometries on the exposed edge (see for example FIG. 24) are developed such as for small carrier plates 14 and recesses for the AFT process.

Figure 6:
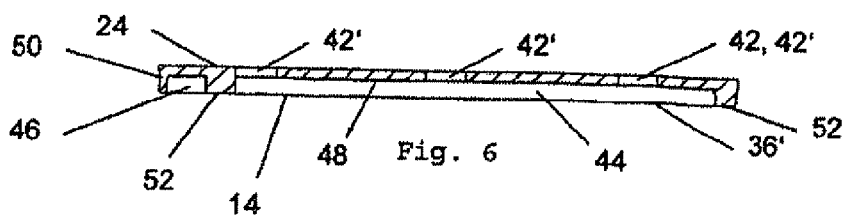
FIG. 6 shows a longitudinal section of the small carrier plate along the line VI-VI of FIG. 2.
Figure 7:
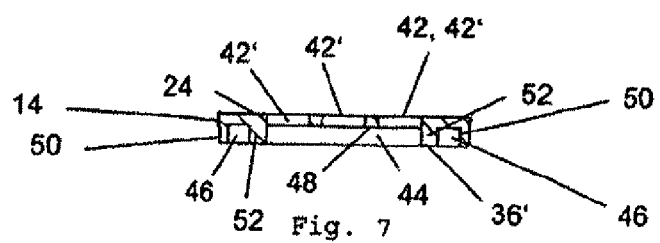
FIG. 7 shows a cross section of the small carrier plate along the line VII-VII of FIG. 2.
Figure 14:
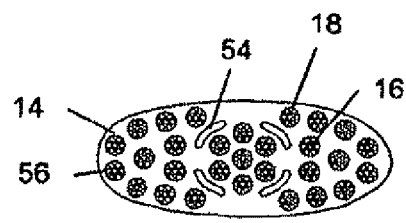
FIG. 14 shows the same representation as FIGS. 2 and 8 of the small carrier plate which is provided with first and second type injection-molded bristles.
Figure 15:
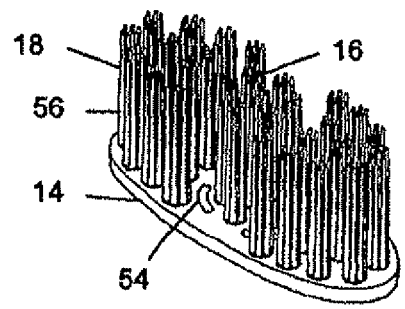
FIG. 15 shows the same representation as FIGS. 3 and 9 of the small carrier plate from FIG. 14 which is provided with first and second type injection-molded bristles.
Figure 16:
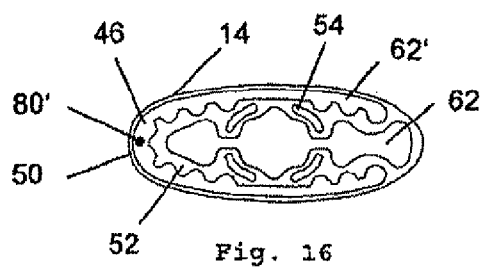
FIG. 16 shows the same representation as FIGS. 4 and 10 of the small carrier plate from FIG. 14 which is provided with first and second type injection-molded bristles.
Figure 17:
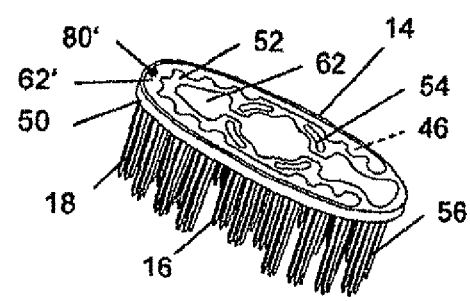
FIG. 17 shows the same representation as FIGS. 5 and 11 of the small carrier plate from FIG. 14 which is provided with first and second type injection-molded bristles.
Figure 18:
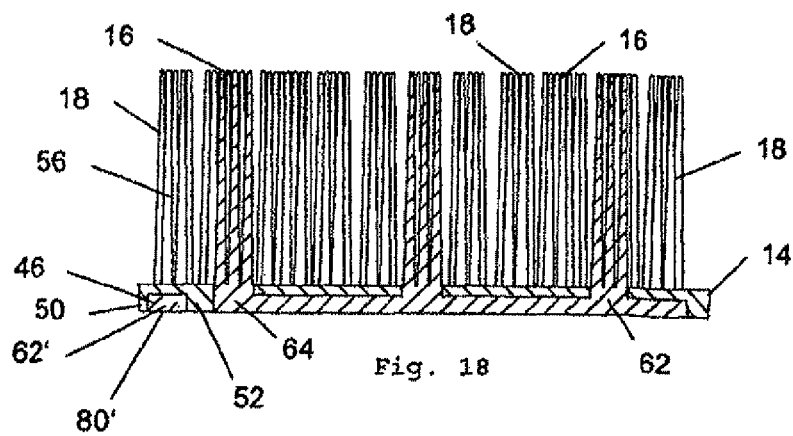
FIG. 18 shows the longitudinal section of the same representation as FIGS. 6 and 12 of the small carrier plate from FIG. 14 which is provided with first and second type injection-molded bristles.
Figure 19:
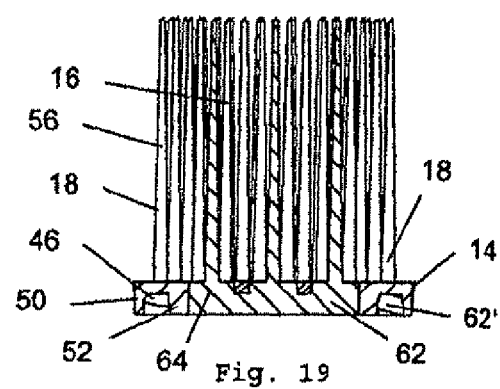
FIG. 19 shows the cross section of the same representation as FIGS. 7 and 13 of the small carrier plate from FIG. 14 which is provided with first and second type injection-molded bristles.
Figure 20:
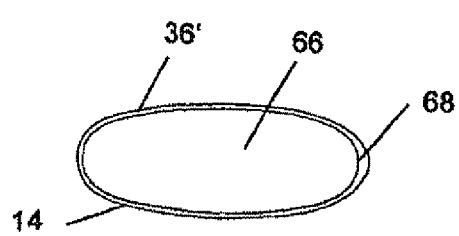
FIG. 20 shows the same representation as FIGS. 2, 8 and 14 of the small carrier plate provided with first and second type injection-molded bristles as well as additionally with flexible massaging and cleaning elements, the flexible material also covering the rear side of the small carrier plate.

In the present case, channel walls 50 (see for example FIG. 6) form the welding support and an offset TPE layer serves for centering the small carrier plate 14 in the trough-shaped recess in the head part 32.

The welding region between the small carrier plate 14 and the head part 32 is preferably kept free of bristle material 62; see for example FIG. 12.

The brush body 26 is produced in the generally known manner using the injection molding method. It can, as in the present exemplary embodiment, consist of one single hard material. However, it can also be produced using the two-component or multiple-component injection molding method. In this case, it is possible to use two or more hard materials or at least one soft material in addition to at least one hard material.

In the exemplary embodiment shown, on the handle part 28 a thumb support 34 is realized on the front side 24' of the brush body 26 and a forefinger support 38 is realized on the rear side 36. Said supports are realized by means of a series of protruding ribs 40.

The method for producing the manual toothbrush 10 shown in FIG. 1 and the design thereof proceed from FIGS. 2 to 26. Reference is made to the introduction further above concerning the materials and the dimensions.

FIGS. 2 to 7 show a small carrier plate 14 which is produced from a hard material using the injection molding method. In the exemplary embodiment shown, the front side 24 thereof is flat.

However, it is also possible for the front side 24 to be in a three-dimensional form and/or to be produced using the two-component or multiple-component injection molding method. In this case, it can be produced, for example, from two different hard materials; however, it is also possible for it to have, for example, two or more portions made of a hard material which are fastened to one another by means of a soft material. It is also conceivable for sleeves, formed from a hard material, to be provided for the injection-molded bristles 16, 18 and said sleeves to be fastened by means of a soft material on the remaining part of the small carrier plate 14 made of hard material.

The small carrier plate 14 shown has passages 42 which extend continuously from the front side 24 to the rear side 36'.

As proceeds from FIGS. 4 to 7, the small carrier plate 14 has distributing channels 44 and 46 which are open toward the rear side 36'. The first distributing channel 44 is associated with the first type injection-molded bristles 16 and the second distributing channel 46 is associated with the second type injection-molded bristles 18. The relevant first passages 42' and second passages 42" extend from the bottom 48 of the first distributing channel 44 or second distributing channel 46 to the front side 24 of the small carrier plate 14.

The second distributing channel 46 extends in a U-shaped manner along the edge of the small carrier plate 14, it being defined radially toward the outside by a first channel wall 50. The second distributing channel is defined radially toward the inside by a second channel wall 52 which, in turn, forms the outermost radial boundary of the first distributing channel 44.

In its front end region, the first distributing channel has a triangular widening, from which three first passages 42' extend in the rounded corners. In the central region of the small carrier plate 14, the first distributing channel 44 has a somewhat circular widening, from which extend seven first passages 42' arranged in the manner of a rosette. In the rear end region, the first distributing channel 44 has a third widening which is realized in an approximately rectangular manner. Five first passages 42' extend from said widening. The mentioned widenings are connected together by means of channel portions 44'—extending in the longitudinal direction of the small carrier plate 14.

The second channel wall 52 has channel wall passages 54, which pass from the rear side 36' through to the front side 24, are associated with the flexible massaging and cleaning elements 20 and extend in the manner of segments about the central widening of the first distributing channel 44.

The second passages 42" are arranged in a row one behind the other along the second distributing channel 46.

FIGS. 8 to 13 show the same representation of the small carrier plate 14 as in FIGS. 2 to 7, the first type injection-molded bristles 16 now having been produced using the injection molding method. Said bristles are combined into bristle bundles 56, each bristle bundle 56 being associated with one of the first passages 42'.

Figure 46:
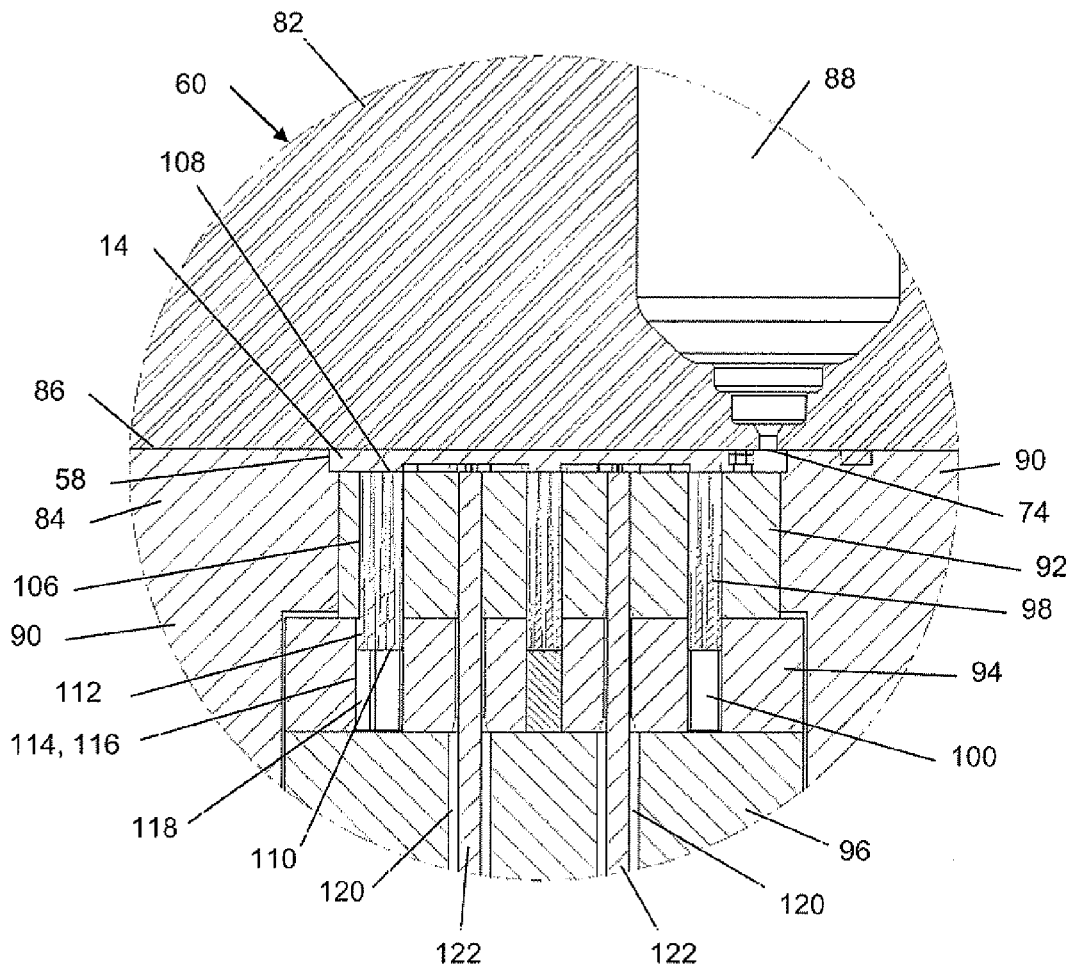
FIG. 46 shows a section through part of an injection molding tool for injecting the injection-molded bristles onto a small carrier plate for a toothbrush according to FIGS. 1 to 25.

To produce the first type injection-molded bristles 16, the small carrier plate 14 is inserted into a carrier cavity 58 of an injection molding tool 60, as is shown in FIG. 46 and is described further below. The bristle material 62 for the first type injection-molded bristles 16 is injected into the first distributing channel 44 where it is distributed and flows through the first passages 42' for forming the first type injection-molded bristles 16.

As can be seen in particular from FIGS. 12 and 13, the first type bristles 16 are realized integrally—i.e. in one piece—with the bristle material 62 present in the first distributing channel 44. In addition, as can be seen from FIGS. 10 to 13, the first distributing channel 44 is filled with the bristle material 62.

The production of the bristle bundles 56 with the first type and second type injection-molded bristles 16, 18 is explained in more detail further below in conjunction with FIGS. 46 to 53 and 67 to 69.

At this point, however, it must already be mentioned that a bristle bundle 56 in the exemplary embodiment shown consists of seven first type injection-molded bristles 16. Said injection-molded bristles 16 stand on the front side 24 of the small carrier plate 14, protruding therefrom. In the exemplary embodiment shown, their exposed part 22 extends from the plane defined by the front side 24, a bristle base 64 which is common to the first type injection-molded bristles of each bristle bundle 56 being realized in the first passages 42'. The length of the exposed part 22 corresponds to the exposed length.

In a preferred manner, the maximum height of the bristle base 64 for first type injection-molded bristles 16 as also for second type injection-molded bristles 18 is as high as the outside edge of the small carrier plate 14 or the first channel wall 50.

FIGS. 14 to 19 show the same representation as FIGS. 2 to 13 of the small carrier plate 14, which is now, however, provided with the second type injection-molded bristles 18 in addition to the first type injection-molded bristles 16. For this purpose, the small carrier plate 14 provided with the first type injection-molded bristles 16 has been inserted into a corresponding cavity of the injection molding tool 60. The bristle material 62' for the second type injection-molded bristles 18 has been injected into the second distributing channel 46, said material having been distributed in said second channel and having flowed through the second passages 42" to form the second type injection-molded bristles 18.

In the present exemplary embodiment, the second distributing channel 46 is filled with the bristle material 62' and the bristle material 62' present in the second distributing channel 46 is connected integrally, i.e. in one piece, to the second type injection-molded bristles 18. Moreover, the second type injection-molded bristles 18 are realized, in this case, identically to the first type injection-molded bristles 16.

The first type injection-molded bristles 16 and the second type injection-molded bristles 18 can differ, for example, by the color of the bristle material 62, 62'. It is also possible for the bristle material 62 to be a different material to the bristle material 62', for example in chemical composition or other characteristics (for example the Shore hardness of the material, the surface quality).

Figure 54:
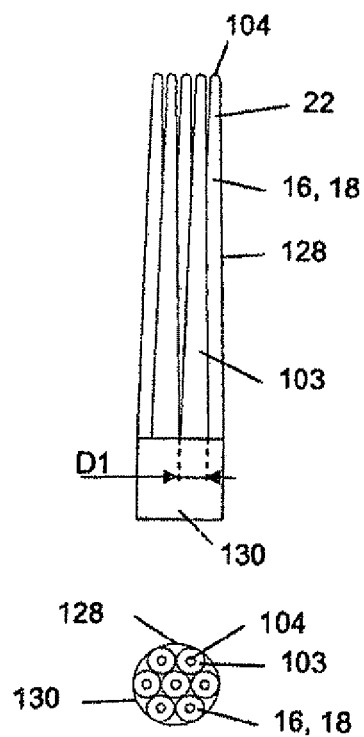
FIG. 54 shows a projection and top view of a first embodiment of an individual bundle of injection-molded bristles.

It is also conceivable for the bristle material 62 and the bristle material 62' to be identical. In addition, it is possible for the first type injection-molded bristles 16 and the second type injection-molded bristles 18 to differ in their dimensions, for example by their length or also by their geometrical development. Examples of different lengths are shown in FIGS. 54 and 55.

FIGS. 20 to 25 show the small carrier plate 14 in the identical representation as FIGS. 2 to 19, said small carrier plate now being provided with the flexible massaging and cleaning elements 20 in addition to the first type injection-molded bristles 16 and the second type injection-molded bristles 18.

To produce the flexible massaging and cleaning elements 20, the small carrier plate 14, which is provided with the first type injection-molded bristles 16 and the second type injection-molded bristles 18, is inserted into a further cavity of the injection molding tool 60 and the relevant soft material 66 for the massaging and cleaning elements 20 is injected into the relevant cavity on the rear side 36' of the small carrier plate. In this case, the soft material 66 is distributed corresponding to the cavity, in the present example on the entire rear side 36' of the small carrier plate 14 as far as up to the circumferential edge 68 which remains free of the soft material 66 and is required, for example, for welding to the brush body 26.

In addition, during the injection molding process the soft material 66 flows right through the channel wall passages 54 and on the front side 24 forms the flexible massaging and cleaning elements 20 which protrude from the small carrier plate 14. In the case of this exemplary embodiment, as an example, they form—in top view—an approximately circular structure which extends around the central seven bristle bundles 56 with first type injection-molded bristles 16 and which has a wavy height contour in order to form the four flexible massaging and cleaning elements 20.

The soft material 66 of the flexible massaging and cleaning elements 20 lies between the channel wall passages 54 on the surface of the small carrier plate 14 or is connected to said small carrier plate on the surface by means of material bonding.

It must be mentioned at this point that it is also conceivable to provide a distributing channel (or several distributing channels) for the soft material 66 (or soft materials 66) in the small carrier plate 14 and to distribute the soft material through said distributing channel to form the flexible massaging and cleaning elements 20 during the injection molding process. In this case, it is possible for the soft material 66 to fill the relevant distributing channel, but, for the rest, to leave the rear side 36' of the small carrier plate 14 free. In this case, corresponding passages in the small carrier plate 14 allow the soft material 66 from the distributing channel to penetrate onto the front side 24 of the small carrier plate 14.

It is possible for the head part 32 of the brush body to be realized in a circular manner and for the small carrier plate 14, which is provided with the injection-molded bristles 16, 18 and the flexible massaging and cleaning elements 20, to be inserted into the head part 32 in such a manner that the soft material 66 lies freely on the rear side 36' of the small carrier plate 14 on the rear side 36 of the manual toothbrush 10. In this case, during the injection molding of the soft material 66, a—bristle-free, i.e. not having bristles—tongue cleaning element, which has for example protruding nubs and/or ribs and/or lamellae, can be formed by means of said soft material on the rear side in the identical injection molding operation, said tongue cleaning element lying freely (similar to the embodiment according to FIGS. 41 to 44).

To complete the picture, it must be mentioned that flexible massaging and cleaning elements 20 and/or second type injection-molded bristles 18 do not necessarily have to be present.

Figure 26:
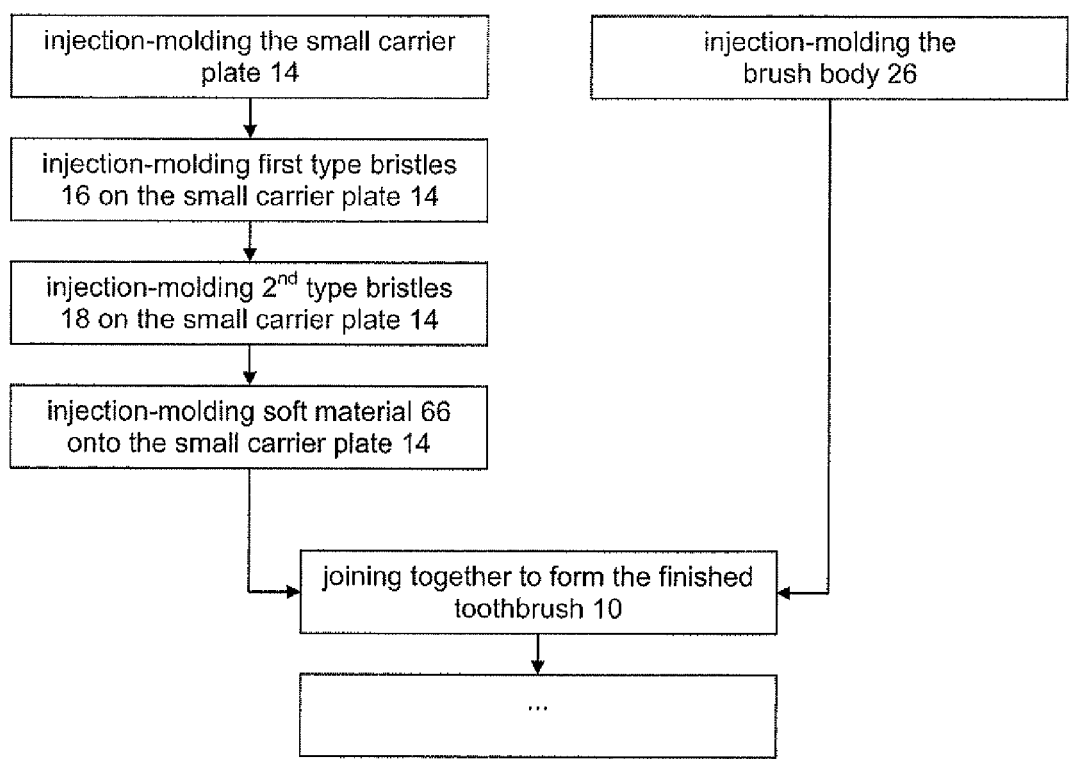
FIG. 26 shows a schematic representation for the production of a toothbrush according to FIG. 1 with a brush body and a small carrier plate according to FIGS. 2 to 25 arranged in the head region thereof.
Figure 33:
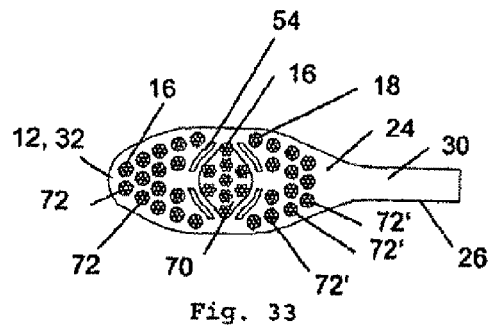
FIG. 33 shows the same representation as FIG. 27 of the part of the brush body shown there provided with first and second type injection-molded bristles.
Figure 34:
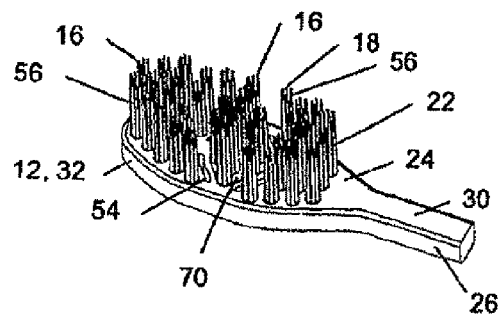
FIG. 34 shows the same representation as FIG. 28 of the part of the brush body shown there provided with first and second type injection-molded bristles.

The correct procedural sequence for producing the manual toothbrush 10 according to FIG. 1, as is explained further above by way of FIGS. 2 to 25, is shown in a flow diagram in FIG. 26.

The small carrier plate 14 is produced by means of injection molding in a first step.

In a second step, the first type injection-molded bristles 16 are injected onto the small carrier plate 14 by means of injection molding by injecting bristle material 62 into the first distributing channel 44.

In a third step, the second type injection-molded bristles 18 are injected onto the small carrier plate 14 by means of injection molding by injecting bristle material 62' into the second distributing channel 46.

In a fourth step, the soft material 66 is injection-molded onto the small carrier plate 14, thereby, in the exemplary embodiment shown, producing the flexible massaging and cleaning elements 20.

Where the distributing channels are physically separated, the bristle materials 62, 62' and the soft material 66 can be injected into the same injection molding cavity at the same time or offset in time.

The brush body 26 is produced separately by means of injection molding. The brush body 26 and the small carrier plate 14, which is provided with the injection-molded bristles 16, 18 and the injection-molded soft material 66 (the massaging and cleaning elements 20), are then joined together. This can occur, for example, by means of manipulators or robots. The two joined-together parts, in this case, are fixedly connected together, for example, by means of welding, in particular ultrasound welding, by means of bonding, or snap-type connections, etc.

As an alternative to this, the small carrier plate 14, which is provided with the injection-molded bristles 16, 18 and the injection-molded soft material 66 (the massaging and cleaning elements 20), can be injected around with the hard and/or soft material of the brush body 26 and in so doing can be non-releasably connected to said brush body.

In further steps, the finished toothbrush 10 can be processed even further, such as being imprinted and packaged.

As mentioned further above, the small carrier plate 14, which is provided with the injection-molded bristles 16, can be supplied directly to the step of "injection molding soft material 66 onto the small carrier plate 14" or the step of "joining together to form the finished toothbrush 10" if no second type injection-molded bristles 18 or no flexible massaging and cleaning elements 20 are provided. In addition, it is also possible to supply the small carrier plate 14, which is provided with the first type injection-molded bristles 16 and the second type injection-molded bristles 18, (directly) to the step of "joining together to form the finished toothbrush 10"; in this case no soft material 66 or no flexible massaging or cleaning elements 20 are injected.

By way of FIGS. 27 to 44, the production of a further embodiment of a manual toothbrush 10 as claimed in the present invention is explained in more detail. The essential difference between the above-described embodiment and the present one is that the bristle carrier 12 is formed by the head part 32 of the brush body 26 itself. This means that the functions and tasks which the small carrier plate 14 had in the preceding exemplary embodiment are now taken over directly by a corresponding body geometry which is incorporated in the brush body 26. In an analogous manner, the characteristics and alternative embodiments described in conjunction with the small carrier plate 14 are also applicable to said variants.

FIGS. 27 to 32, corresponding to FIGS. 2 to 7, show the bristle carrier 12 which is formed by the head part 32 of the brush body 26. Only the head part 32 and a portion of the neck part 30 are shown of the brush body 26. The remaining portion of the neck part 30 together with the handle part 28 is not shown; the development of said parts, however, is generally known.

The bristle carrier 12, i.e. the head part 32, has continuous, circular passages 42 from the front side 24, visible in FIG. 27, to the rear side 36 which is located opposite thereto. In addition, in the central region there is a single passage 70 which, in this case, is approximately in the form of an oval which extends transversely with respect to the longitudinal extension of the manual toothbrush 12. In addition, there are four channel wall passages 54 which are arranged between the single passage 70 and the passages 42 distributed in the circumferential direction of the single passage 70 at a spacing from said single passage.

In addition, it can be seen in FIGS. 28 to 32 that a first distributing channel 44, which is open toward the rear side 36, extends from the single passage 70.

The association of the first passages 42' with the first distributing channel 44 and of the second passages 42" with the second distributing channel 46 can be seen from FIGS. 29 and 30, which show the rear side 36 of the head part 32.

The first distributing channel 44 extends from the single passage 70 centrally and in the longitudinal direction on both sides of the brush body 26 and is widened, on the one side, in an end region facing the free end of the head part 32 and, on the other side, in an end region of the head part 32 facing the neck part 30. Accordingly, the three rows 72 of passages 42, which extend transversely with respect to the longitudinal direction and face the free end, form the first passages 42'. In addition, the two rows 72', which also extend transversely with respect to the longitudinal direction and lie in the lateral end region in the neck part 30, also form first passages 42'.

In the case of said embodiment, in the transition region between the neck part 30 and the head part 32, the brush body 26 additionally has an injection channel 74 which is open toward the rear side 36. Said injection channel is fluidically connected to the first distributing channel 44 by means of an injection passage 76 which extends in the interior of the brush body 26.

In addition, the head part 32 has two second distributing channels 46. When viewed in the longitudinal direction, said channels extend laterally outside the single passage 70 and widen in their end region facing the free end and in their end region facing the neck part 30 in such a manner that in each case three passages form second passages 42". The channel wall passages 54, which separate the second distributing channels 46 from the single passage 70 and the first distributing channel 44, are arranged in the second channel wall 52 between said widened regions of the second distributing channels 46 and the single passage 70. Both the first distributing channel 44 and the two further distributing channels 46 are defined radially on the outside by the first channel wall 50, which extends along the lateral periphery of the head part 32.

It must be mentioned at this point that the second channel wall 52 is offset with reference to the plane of the rear side 36 of the head part 32 defined by the first channel wall 50, i.e. the first channel wall 50 forms the outside contour.

In the exemplary embodiment shown, the bottoms 48 of the distributing channels 44, 46 lie in a common plane and the height of the second channel wall 52 is less than the height of the first channel wall 50.

FIGS. 33 to 37 show the bristle carrier 12 which is provided with the first type injection-molded bristles 16 and the second type injection-molded bristles 18. To produce said bristles, the brush body 26, which is shown in FIGS. 27 to 32 and is produced beforehand using the injection molding method, is inserted into the corresponding carrier cavity 58 of the injection molding tool 60. The bristle material 62 required for forming the first type injection-molded bristles 16 is injected into the injection channel 74. The bristle material 62 flows from there through the injection passage 76 into the first distributing channel 44 and from said channel through the first passages 42' into the bristle cavities 102 (see FIG. 46) for forming the first type injection-molded bristles 16.

At the same time or in a second injection molding step, the bristle material 62' used to form the second type injection-molded bristles 18 is injected into the two second distributing channels 46. The bristle material 62' is distributed in the second distributing channels and flows right through the second passages 42" into the bristle cavities 102 for forming the second type bristles 18.

The bristle material 62 and the bristle material 62' fill the first distributing channel 44 or the two second distributing channels 46 between the first and second channel walls 50, 52, as can be seen in particular from FIGS. 35 to 38.

The first type injection-molded bristles 16 are realized integrally in the first distributing channel together with the bristle material 62. This also applies to the second type injection-molded bristles 18 and the bristle material 62' which is present in the second distributing channels 46.

To complete the picture, it must be mentioned that the bristle material 62 which flows through the central single passage 70 toward the front side 24 is used to form several bristle bundles 56 of first type injection-molded bristles 16, in the exemplary embodiment shown nine bristle bundles 56, the bristle base 64 formed in the single passage 70 being common to said bristle bundles 56.

Bristle bases 64, from which extend relevant bristle bundles 56 of, for example, seven first type injection-molded bristles 16 or second type injection-molded bristles 18, are also formed in the first passages 42' and the second passages 42".

In addition, it must be noted that both the first type injection-molded bristles 16 and the second type injection-molded bristles 18 of some bristle bundles 56 are shorter in the length of their exposed part 22 than the bristles 16, 18 of other bristle bundles 56; compare also FIGS. 54 to 57.

FIGS. 39 to 44 show the bristle carrier 12 which is provided with the first and the second type injection-molded bristles 16, 18—compare FIGS. 33 to 38—the (bristle-free) flexible massaging and cleaning elements 20 and on the rear side 36 a (bristle-free) tongue cleaning element 78, in this case having protruding nubs, now also being formed from the soft material 66. The bristle materials 62 and 62' can obviously form, additionally or just per se, part of the tongue cleaning element 78.

The bristle carrier 12 provided with bristles is inserted into a corresponding cavity of the injection molding tool 60 and the soft material 66 is then injected into the trough-shaped space which is defined on the circumferential side by the first channel wall 50 and on the bottom side by the second channel wall as well as in the bristle material 62 and 62'. Said trough-shaped space is filled as far as up to the rear end of the first channel wall 50, nubs which protrude with reference to said plane forming the tongue cleaning element 78. Said tongue cleaning element can also be formed by lamellae or other types of projections.

When the soft material 66 is injected, it flows right through the channel wall passages 54 in order to form the flexible massaging and cleaning elements 20 which protrude on the front side 24. In the design shown, massaging and cleaning elements 20 are formed on the front side 24' and at the same time tongue cleaning elements 78 are formed on the rear side 36 of the toothbrush 10. They are connected together in an integral manner. In addition, it is also possible for the same soft material 66, along with the named elements in the head part 32, also to form elements in the neck part 30 and/or handle part 28, for example elements in the region of the forefinger support 38 or the thumb support 34.

In the exemplary embodiment shown, the free length of the flexible massaging and cleaning elements 20 is shorter than the exposed length, i.e. the exposed part 22 of the shorter injection-molded bristles 16, 18. The length ratios, however, can also be realized in another manner.

Figure 35:
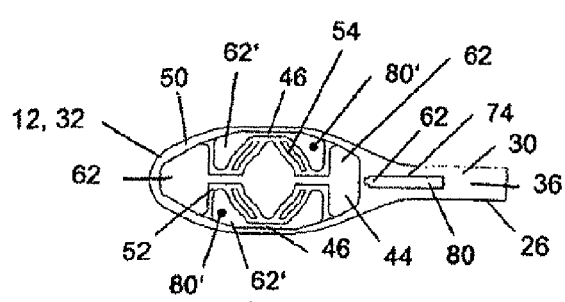
FIG. 35 shows the same representation as FIG. 29 of the part of the toothbrush body provided with first and second type injection-molded bristles.
Figure 36:
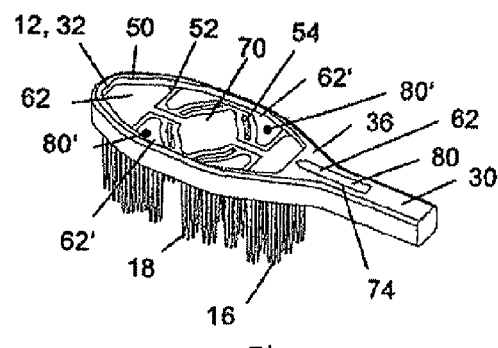
FIG. 36 shows the same representation as FIG. 30 of the part of the toothbrush body shown there provided with first and second type injection-molded bristles.
Figure 37:
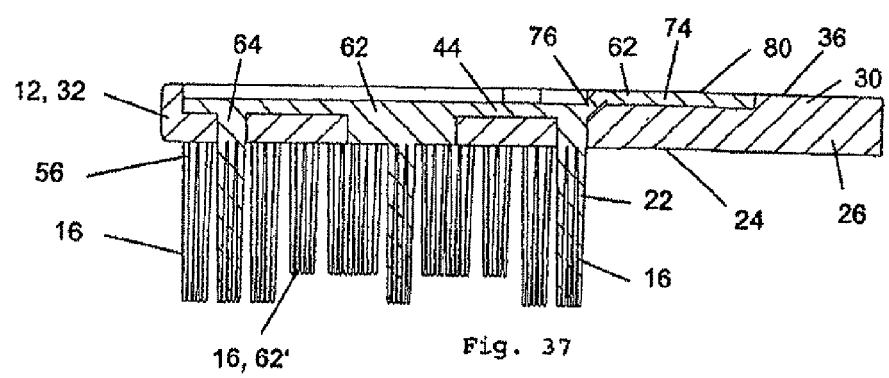
FIG. 37 shows the longitudinal section of the same representation as FIG. 31 of the part of the brush body provided with first and second type injection-molded bristles.
Figure 38:
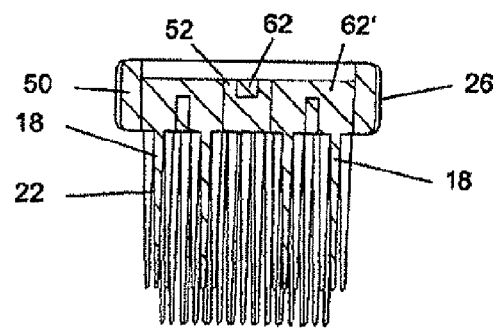
FIG. 38 shows the cross section of the same representation as FIG. 32 of the part of the brush body provided with first and second type injection-molded bristles.
Figure 39:
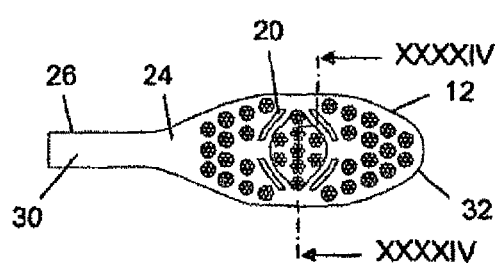
FIG. 39 shows the same representation as FIGS. 33 and 37 of the part of the brush body shown there provided with first and second type injection-molded bristles and flexible massaging and cleaning elements.

In the present exemplary embodiment, the injection point 80 for the first bristle material 62, as shown in FIGS. 35 to 37, is situated in the region of the injection channel 74.

The injection points 80' for the second bristle material 62' are arranged in the region of the three passages 42" offset with regard to the second passages 42". They are preferably arranged diagonally with reference to the single passage 70; this is produced from the design of the injection molding tool 60.

Also in the case of the embodiment described further above and shown in FIGS. 1 to 25, the injection points 80 for the bristle material 62 and 80' for the bristle material 62' are arranged offset with reference to the first passages 42' and second passages 42".

Figure 45:
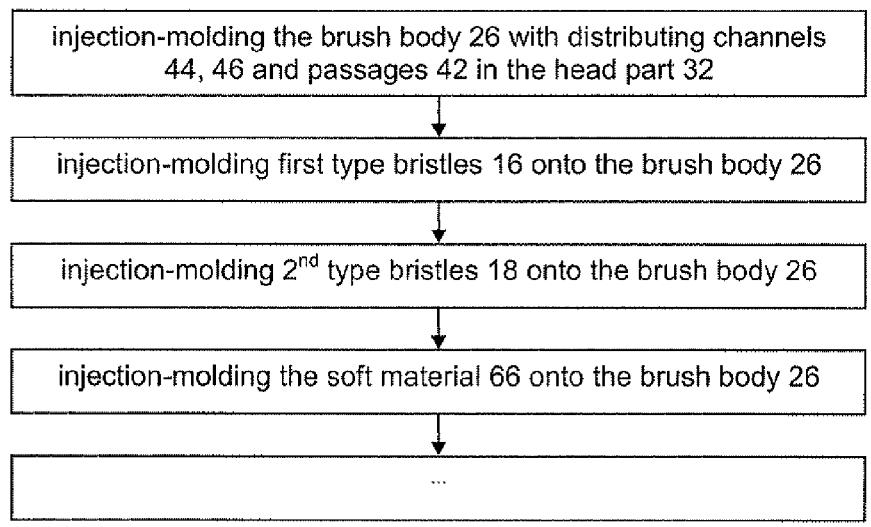
FIG. 45 shows a flow diagram for producing a toothbrush according to FIGS. 27 to 44.

FIG. 45 shows the steps for producing a manual toothbrush 10, as is described above and shown in FIGS. 27 to 44.

The brush body 26 with the distributing channels 44, 46 and the passages 42, 42' is produced by means of injection molding in a first step. In this case, a hard material is used and at least the skeleton of the handle part 28 and also of the head part 32 are injected.

The first type injection-molded bristles 16 are produced by means of injection molding in a second step by injecting the bristle material 62 into the first distributing channel 44 or into the injection channel 74.

The second type injection-molded bristles 18 are produced by means of injection molding in a third step by injecting the bristle material 62' into the second distributing channels 46.

In a fourth step, the soft material 66 is injected onto the brush body 26 to form the flexible massaging and cleaning elements 20 and the tongue cleaning element 78. In addition, said soft material 66 can also be used for the purpose of developing further parts in the brush body 26, for example in the neck part 30, on the thumb support 34, the forefinger support 38 or in the handle part 28.

In further steps which are not listed in a detailed manner, the manual toothbrushes 10 can be imprinted and packaged.

It is also possible to inject the first type injection-molded bristles 16 and the second type injection-molded bristles 18 in the same method step. In this case, it is a prerequisite that there is no direct contact between the two relevant materials. This works when the two bristle materials 62, 62' are clearly separated by the channel walls 50, 52.

It is also possible in the present case to dispense with a soft material 66 and to develop a toothbrush only from first type injection-molded bristles 16 or only from second type injection-molded bristles 18, i.e. without any flexible massaging and cleaning elements and without a tongue cleaning element 78.

A toothbrush 10 produced in the manner as described in FIG. 45 consists of at least two plastics material components, a hard material for the handle part 28, the neck part 30 and the head part 32 as well as a bristle material for producing the injection-molded bristles.

In addition, it is also possible to inject further injection-molded bristles, for example third type to $x^{th}$ type or also to use several soft materials. This is the case for all design variants.

The more components used for the production of the toothbrush, the more possibilities there are for developing the bristle bundles and handle parts.

FIG. 46 shows a cross section through part of an injection molding tool 60 for producing toothbrushes as claimed in the present invention. That part of the injection molding tool 60 which serves for producing the injection-molded bristles 16, 18 is shown.

In a known manner, the injection molding tool 60 has a fixed first tool part 82 and a second tool part 84 which is displaceable in relation thereto. The separation plane between the two tool parts 82, 84 is identified by way of the reference 86.

The two tool parts 82, 84 define a carrier cavity 58 which serves for accommodating the bristle carrier 12 (not provided with bristles). In the embodiment shown, the bristle carrier 12 is formed by the small carrier plate 14 which serves for producing a toothbrush according to FIGS. 1 to 25.

The production of a toothbrush according to FIGS. 27 to 44 operates in an identical to similar manner. The head part 32 is placed in the correspondingly formed carrier cavity 58.

A hollow space 88 for the nozzle runs right through the first tool part 82. Said generally known nozzle is not shown here; it is supplied by the injection molding machine with the relevant bristle material 62 or 62' for producing the first type injection-molded bristles 16 or the second type injection-molded bristles 18. The nozzle in the hollow space 88 opens out into the carrier cavity 58 at the relevant injection point 80 or 80' such that the bristle material 62 or 62' flows into the associated first distributing channel 44 or second distributing channel 46.

The second tool part 84 is constructed in multiple parts. It has a base plate 90 in which a defining body 92 which defines the carrier cavity 58, a guide block 94 and a support body 96 are arranged. The support body 96 abuts against the guide block 94 and holds the same in abutment against the defining body 92 on its side remote from the carrier cavity 58, so that in the end the small carrier plate 14 is clamped in the carrier cavity 58 and in this way closed channel contours are formed by the distributing channels 44, 46 and the corresponding metal counterparts. In this case, it is possible to reinforce the clamping and consequently the sealing for example by way of oversizing the height of the small carrier plate 14 compared to the space in the carrier cavity 58.

In addition, the second tool part 84 has one first tool insert 98 and one second tool insert 100 per bristle bundle 56 to be injection-molded. A continuous bristle cavity 102, which serves for forming the bristle stem 103 of the bristles 16, 18 and which connects to the carrier cavity 58 such that the bristle material 62 or 62' supplied to said carrier cavity is able to flow right into the bristle cavities 102 through the passages 42 or 42' or 42'', is formed on the first tool insert 98 per first type bristle to be injection-molded or per second type bristle to be injection-molded 18.

The second tool insert 100 connects on the side of the first tool insert 98 facing away from the carrier cavity 58. Said second tool insert serves for forming the bristle cap 104, i.e. the free, usage-side end region 104 of the relevant injection-molded bristle 16, 18. The bristle cap 104 is only identified in a corresponding manner in FIGS. 54 to 57, representing all the rest of the embodiments.

The first tool insert 98 is arranged in an associated, continuous insert passage 106 of the defining body 92, penetrates the latter and in the closed state of the injection molding tool 60 abuts against the bristle carrier 12 by way of its end face 108 facing the bristle carrier 12. By way of an end region 112, which connects to the end face 110 opposite the end face 108, the first tool insert 98 engages in a guide recess 114 of the guide block 94. The second tool insert 100 is also arranged in said guide recess 114. By way of its end remote from the first tool insert 98, the second tool insert 100 abuts against the support body 96.

Figure 53:
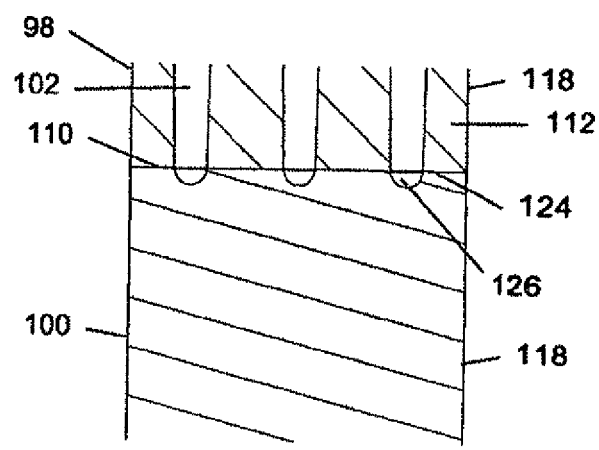
FIG. 53 shows a longitudinal section through part of the second tool insert abutting against the first tool insert.

The guide recess 114—in cross section—has a polygonal contour 116, in a preferred manner a four-edged contour, in order to guide the first tool insert 98 and second tool insert 100 in a precisely aligned manner one on top of the other, as is shown in FIG. 53. For this purpose, the first tool insert 98 has a corresponding counter contour 118 in the end region 112 and the second tool insert 100 has a corresponding counter contour 118 as is described further below by way of FIGS. 47 to 53.

The precise alignment between the cap cavities 126 and the bristle cavities 102 is very important so that the forming of undercutting geometries as a result of centering the two cavities in a non-precise manner or the bristle cap 104 being offset in relation to the remaining part of the injection-molded bristles 16, 18 can be avoided. For example, when being removed from the mold, this would lead to the bristles 16, 18 being elongated until the material portion could be released from the undercut.

In the end, the defining body 92, the guide block 94 and the support body 96 have ejector passages 120 which are penetrated by ejection pins 122 and, with the injection molding tool 60 open, serve for ejecting the bristle carrier 12, which is provided with first type injection-molded bristles 16 and second type injection-molded bristles 18, out of the carrier cavity 58.

To complete the picture, it must be mentioned that the defining body 92 is guided precisely in the base plate 90.

FIGS. 47 to 50 show the one-piece, first tool insert for producing a bristle bundle 56, which, in this case, consists of seven injection-molded bristles 16 or 18. Other numbers of bristles per tool insert 98 are obviously also possible. The bristle stem of the injection-molded bristles 16, 18 is formed in the bristle cavity 102 using the tool insert 98.

In the end region 112, which extends, for example, approximately over 20% of the entire length of the first tool insert 98, the first tool insert 98 has a square cross section as the counter contour 118. For ventilation purposes, the corners of the counter contour 118 are preferably broken, preferably by a 45° chamfering or a corresponding rounding of the corners. The flat sides of the counter contour 118, however, serve the guiding process in the guide recess 114.

The first tool insert 98 has a circular cross section from the end region 112 as far as up to the end face 108. In a corresponding manner, the insert passages 106 in the defining body 92 are also realized with a circular cross section, it being possible to have a thin gap between the first tool insert 98 and the second tool insert 100 for ventilation purposes.

The end face 108 and the further end face 110 are flat. The bristle cavities 102 are removed in a continuous manner from the end face 108 to the further end face 110 on the first tool insert 98. In the exemplary embodiment shown, these are circular and are tapered from the end face 108 to the further end face 110. The dimensions correspond to the measurements specified in the introduction for the injection-molded bristles 16 or 18.

In a preferred manner, a powder-metallurgical steel is used for the first tool insert 98 to produce the bristle cavities 102, which are very small in cross section and extremely long with reference to the small cross section. In a first step, one continuous hole per bristle cavity 102 can be realized in said first tool insert by means of laser beam machining, through which hole an electric discharge machining wire can be inserted in the next step in order to erode or expand the hole subsequently to the desired form of the bristle cavity 102 using the electric discharge machining method (wire eroding). The production method for the bristle cavities 102 has a reason, which is why the cavities for the injection-molded bristles 16, 18 are constructed in two parts.

By means of wire eroding it is not only also possible to realize the bristle cavities 102 with circular cross sections but also possible are polygonal, oval or even star-shaped cross sections which can also have a twist over their length, if desired. The crucial point when shaping the courses of the cross sections is to ensure that removal from the mold or forced removal from the mold is still possible.

FIGS. 51 and 52 show the second tool insert 100 which serves for forming the tip of the injection-molded bristles 16 or 18, referred to as the bristle cap 104. The cylindrical, one-piece second tool insert 100 has the same counter contour 118 as the first tool insert 98. The edges are rounded in the exemplary embodiment shown. As the counter contours 118 on the first and on the second tool insert 98 and 100 are identical, said two parts can be precisely guided, aligned precisely one on top of the other, in the guide block 94 by means of their polygonal contour 116; see also FIG. 53.

On its end face 124 facing the first tool insert 98, the second tool insert 100 has cap cavities 126, which extend from said end face 124 and are flush with the associated bristle cavities 102 of the first tool insert 98, as shown in FIG. 53. The cap cavities 126 are formed corresponding to the desired form of the tip of the injection-molded bristles 16, 18 and, in a preferred manner, the transition from the bristle cavities 102 to the cap cavities 126 is continuous. In the exemplary embodiment shown, the form of the cap cavities 126 is shaped in the manner of a spherical cup.

For technical demolding reasons, however, it is also possible to develop the transition in a non-continuous manner and to design the cap cavities 126 with a somewhat narrower diameter than the diameters of the bristle cavities 102 in the region of the end face 110. Consequently, the undercutting can be completely avoided. This means for the diameter or the cross sectional geometry of the cap cavity 126 on the end face 124 that at the maximum it is the same size as the corresponding geometry of the bristle cavities 102 in the region of the end face 110, however it is preferably smaller than this.

In the exemplary embodiment shown, one central injection-molded bristle 16, 18 and around this six further injection-molded bristles 16, 18, which are distributed uniformly along a circle, are injected per bristle bundle 56. The longitudinal axes of the bristle cavity 102 of the central injection-molded bristle and of two bristle cavities 102 of the further injection-molded bristles lie in a central plane which extends parallel to two sides of the counter contour 118 which are located opposite one another.

In a preferred manner, one central cap cavity 126 and around this twelve further cap cavities 126, which are distributed uniformly on the named circle, are realized on the second tool insert 100, the axes of the central cap cavities lying at right angles with respect to one another and extending parallel to and centrally with respect to the counter contour. The advantage of said embodiment is that no attention has to be paid to the rotational position when the second tool insert 102 is inserted into the guide recess 114. Nevertheless, it is also possible to realize the same number of cap cavities 126 as bristle cavities 102.

This same solution is also possible where there is a different number of bristles 16, 18 in a bristle bundle 56.

FIG. 53 shows the two tool inserts 98, 100 ready to be injection-molded, enlarged compared to FIGS. 47 to 52. The separation plane between the two tool inserts 98, 100 also serves for ventilating the bristle cavities 102 and the cap cavities 126 during the injection molding process. It must be mentioned, moreover, that the second tool insert 100 can be produced from a different steel to the first tool insert 98, in particular a cheaper one.

Figures 67, 68:
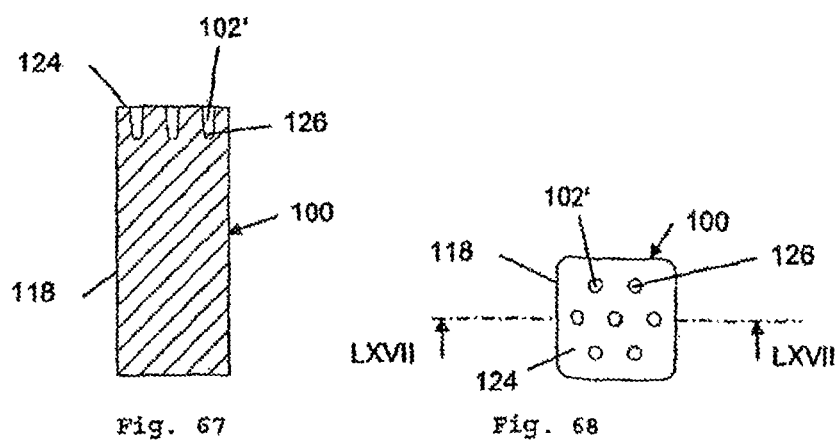
FIG. 67 shows a longitudinal section along the line LXVII-LXVII of FIG. 68 of a further design variant of a second tool insert.
FIG. 68 shows a top view of the second tool insert from FIG. 67.

FIGS. 67 and 68 show a further embodiment of a second tool insert 100 which serves for forming the tip of the injection-molded bristles 16 or 18, referred to as the bristle cap 104. The characteristics and functionalities of the second tool insert 100 shown in said figures correspond to those of the embodiment shown in FIGS. 51 and 52 and described further above, with the exception of the geometry or the division of the cavity between the bristle cavities 102 and the cap cavities 126; cf. also FIG. 69.

The cap cavities 126 are formed corresponding to the desired form of the tip of the injection-molded bristles 16, 18. Contrary to the cap cavities 126 shown in FIGS. 51 and 52, the cavities of the second tool insert shown in FIGS. 67 and 68 are greater or longer (measured along the longitudinal axis of the injection-molded bristle or of the second tool insert). This means that a part 102' of each bristle cavity 102 is also formed in the cavities of the second tool insert 100 along with the cap cavities 126. The transition point between the first and second tool inserts 98 and 100 (the separation plane) is no longer arranged at the transition between the bristle stem 103 and the bristle cap 104, but is rather in the region of the bristle stem 103. Part of the bristle stem 103 is formed in the second tool insert 100.

The advantage of dividing the cavity for the forming of the injection-molded bristles 16, 18 in this manner is that even where the diameters of the bristle stem 103 are small, it is possible to achieve a sturdy production process (wire eroding) on the side of the bristle caps 104 as the end diameter of the first tool insert 98 (with the injection-molded bristles 16, 18 and consequently the corresponding cavities having the same form) becomes larger in this way. A sturdy production process also means, in this case, that the round cross section of the injection-molded bristles 16, 18 is more precise. The finer structures can then be brought into the second tool insert 100 using other methods.

Figure 69:
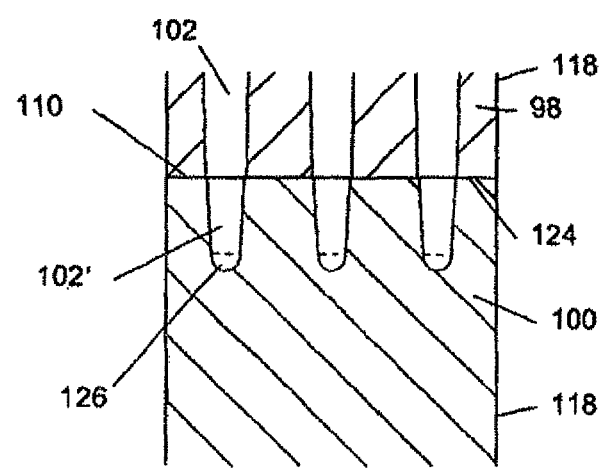
FIG. 69 shows a longitudinal section through part of the second tool insert from FIGS. 67 and 68 abutting against the first tool insert.

FIG. 69 shows an enlarged representation of the two tool inserts 98, 100 from FIGS. 67 and 68, ready to be injection-molded, in the region of the separation plane. In this case, it can clearly be seen that part of the bristle stem 103—corresponding to the part 102' of the bristle cavity 102—is formed by the second tool insert 100.

The end diameter varies as regards size in the same manner as already specified.

Using an injection molding tool 60, as shown and described in conjunction with FIGS. 46/47 to 53 and 67-69, individual bundles 128 with injection-molded bristles 16, 18 can also be produced. Only the carrier cavity 58 has to be realized in a different manner for this purpose by no longer being realized for the accommodation of the bristle carrier 12 or the small carrier plate 14, but having a form which corresponds to the desired bundle stem 130, for example in the shape of a circular cylinder as shown in FIGS. 54 to 57.

By means of the correspondingly developed nozzle in the hollow space 88, the bristle material 62, 62' is injected into the carrier cavity 58, which is realized as a bundle stem cavity, from where the bristle material passes into the bristle cavities 102 of the first tool insert 98 and into the cap cavities 126 of the second tool insert 100 for forming the injection-molded bristles 16, 18.

Obviously, it is possible to produce several individual bundles 128 in one single operating cycle when the injection molding tool 60 is provided with several first and second tool inserts 98, 100 and, for example, the first tool part 82 has a distributing channel which extends from the nozzle in the hollow space 88 and leads to the individual carrier cavities 58 which serve for producing the bundle stems 130; or several nozzles are provided generally in the injection molding tool 60.

Figure 54A:
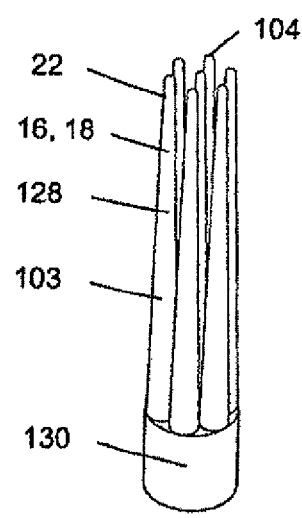
FIG. 54a shows a perspective top view of the first embodiment of the individual bundle.

The individual bundle 128 shown in FIGS. 54 and 54*a* has the bundle stem 130 and seven injection-molded bristles 16, 18 which protrude from said bundle stem. Once again, one central injection-molded bristle and distributed around this the remaining six injection-molded bristles are provided. The injection-molded bristles 16 or 18, i.e. their longitudinal axes, are aligned parallel with respect to one another.

The diameter of the bundle stem 130 corresponds to a multiple of the diameter D1 of a single bristle 16, 18 at the point it exits out of the bundle stem 130. The diameter D1 of the bristle stem 103 and consequently of the injection-molded bristles 16, 18 on the bristle-carrier-side end is only shown in FIG. 54 for reasons of better clarity. The diameter of the bundle stem 130 in relation to the individual bristle is between 2:1 and 6:1, preferably between 2:1 and 4:1.

The height of the bundle stem 130 is between 1.5 mm and 2.5 mm, preferably between 1.7 mm and 2.1 mm.

The individual bundle 128 shown in FIGS. 55 and 55*a* is realized in an identical manner to that according to FIGS. 54 and 54*a*, just the length of the injection-molded bristles 16, 18 being longer; the conicity of the injection-molded bristles 16, 18 is correspondingly adapted to be smaller.

Possible dimensions for individual bundles 128 are specified in the introduction. The same materials as for the remaining embodiments are also used as bristle materials 62, 62' in this case and these are also specified in the introduction.

If, after the injection molding of the individual bundles 128, but also of the bristle bundles 56, the cooling process is carried out in such a manner that the bundle stem 130 or the bristle base 64 cools down slower in the center than radially on the outside, this leads to the bundle stem 130 contracting along the center longitudinal axis of the bristle bundle 56. The exit face of the injection-molded bristles 16, 18 is curved inward in the shape of a sphere such that the outside injection-molded bristles 16, 18, which are still aligned parallel with respect to one another in the injecting molding tool 60, as shown in FIGS. 54, 54*a* and 55, 55*a*, move toward one another by way of their free ends, as is shown in FIGS. 56, 56*a* and 57, 57*a*. The injection-molded bristles 16, 18 form a quasi closed rosette, as the top views show; the maximum being that they move toward one another so much that their free ends contact one another.

The individual bundles 128 can be used, for example, in the subsequently described manner. Several individual bundles 128 are produced in the same injection molding tool. They can be connected, for example, by their injection channels or can also be produced separately. They can then be assembled in the corresponding products and fastened therein. In this case, it is possible to adapt the geometry of the bundle stems 130 so that the assembly and fastening can be effected in an optimized manner; for example, by means of snap-type lugs for locking into brush bodies or also by means of circumferential contours for welding, etc. The individual bundles 128 can be fixed on a brush body so as to be movable or non-movable.

Figure 58:
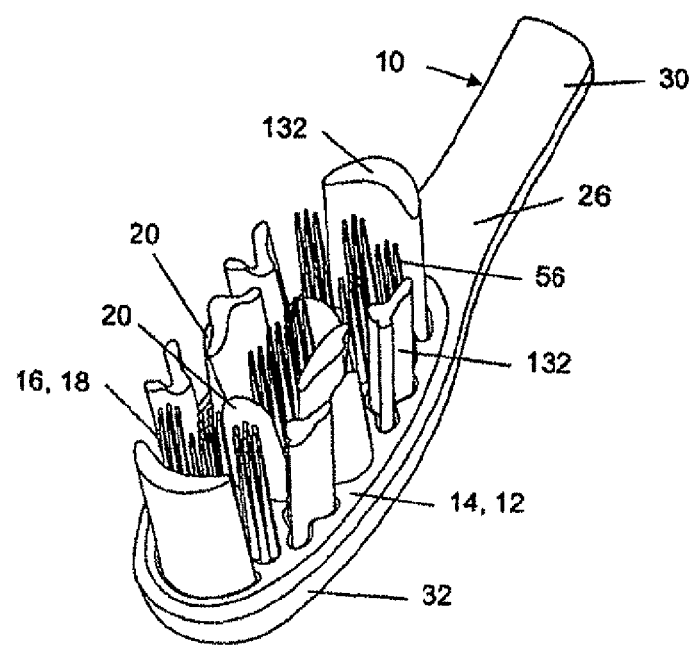
FIG. 58 shows a perspective representation of part of a toothbrush as claimed in the invention with a small carrier plate which is fastened on the toothbrush body and is provided with injection-molded bristles, flexible massaging and cleaning elements and with conventional bristles attached using the AFT method.
Figure 59:
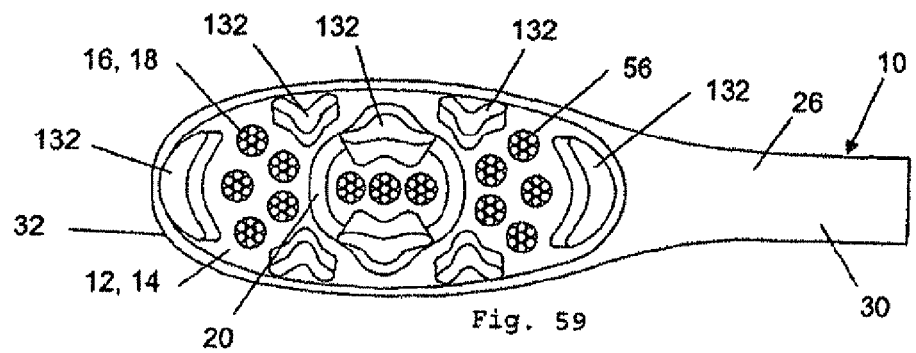
FIG. 59 shows a top view of the toothbrush according to FIG. 58.
Figure 60:
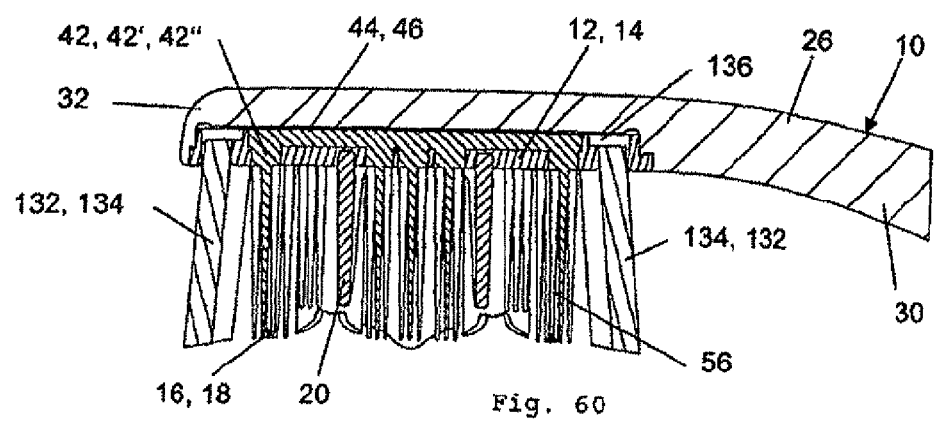
FIG. 60 shows a longitudinal section through the toothbrush according to FIGS. 58 and 59.

FIGS. 58 to 60 show the head part 32 and the neck part 30 of a further manual toothbrush 10 as claimed in the present invention. Once again, first type injection-molded bristles 16 and, where applicable, second type injection-molded bristles 18 made of the relevant bristle material 62 or 62' and (bristle-free) flexible massaging and cleaning elements 20 made of the soft material 66 are injected on the small carrier plate 14, in the same manner as is shown and described further above in conjunction with the embodiment according to FIGS. 1 to 25. The description will not be repeated for reasons of readability; the statements made above are also consequently applicable in an unrestricted manner to the embodiment shown in FIGS. 58-60. The small carrier plate 14 is additionally provided with further bristle bundles 132 made of extruded, conventional bristles 134 fastened thereon.

To produce a toothbrush 10 of this type, the small carrier plate 14 can first of all be provided with the extruded, conventional bristles 134 which form the further bristle bundles 132, the injection-molded bristles 16 or 18 then being produced and afterwards the (bristle-free) flexible massaging and cleaning elements 20 being injection-molded.

The in-mold method (IAP or IMT) presents itself above all for this purpose. In this case, for anchoring on the small carrier plate 14 the extruded, conventional bristles 134 are injected around in the injection molding tool with the hard material and/or soft material of the small carrier plate 14 on their end portion remote from the usage side. The small carrier plate 14, as described beforehand, is then provided with injection-molded bristles 16, 18 and (bristle-free) flexible cleaning and massaging elements 20.

However, it is also conceivable for the further bristle bundles 132 made of extruded, conventional bristles 132 to be inserted last into the bristle carrier 12, or the small carrier plate 14. This means that first of all the injection-molded bristles 16, 18 and where applicable the (bristle-free) flexible massaging and cleaning elements 20 are injection molded in the manner already described before the extruded, conventional bristles 134 are inserted into the bristle carrier 12 or the small carrier plate 14 (using the AFT method or anchor punching method).

To produce the further bristle bundles 132 made of extruded, conventional bristles 134 using the AFT method, conventional bristles 134 are inserted through the relevant continuous passages or recesses of the small carrier plate 14 and the end regions of the extruded, conventional bristles 134 on the rear side 36' of the small carrier plate 14 are then melted in order to realize a melt carpet 136 for fastening on the small carrier plate 14.

Figure 61:
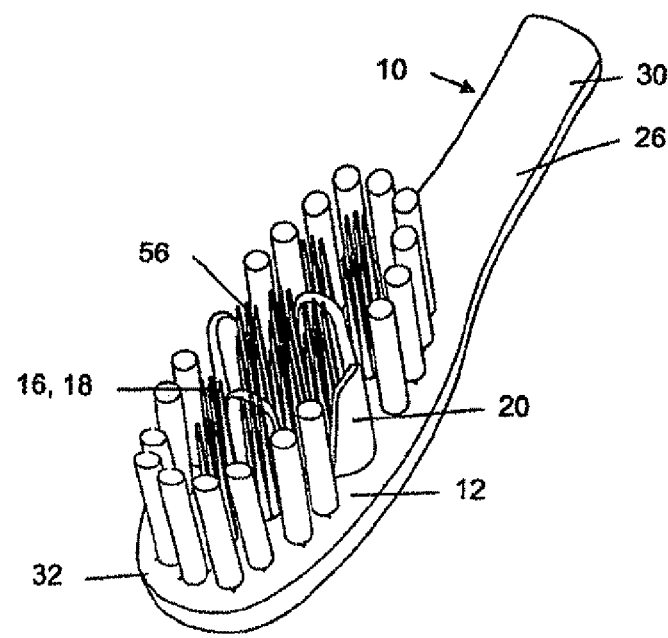
FIG. 61 shows a perspective top view of a further embodiment of a toothbrush as claimed in the invention, where the toothbrush body is provided with injection-molded bristles, flexible massaging and cleaning elements and with punched conventional bristles.
Figure 62:
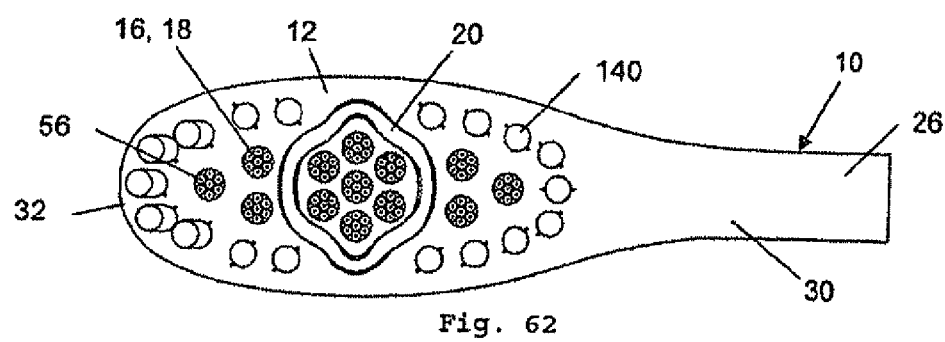
FIG. 62 shows a top view of the toothbrush according to FIG. 61.
Figure 63:
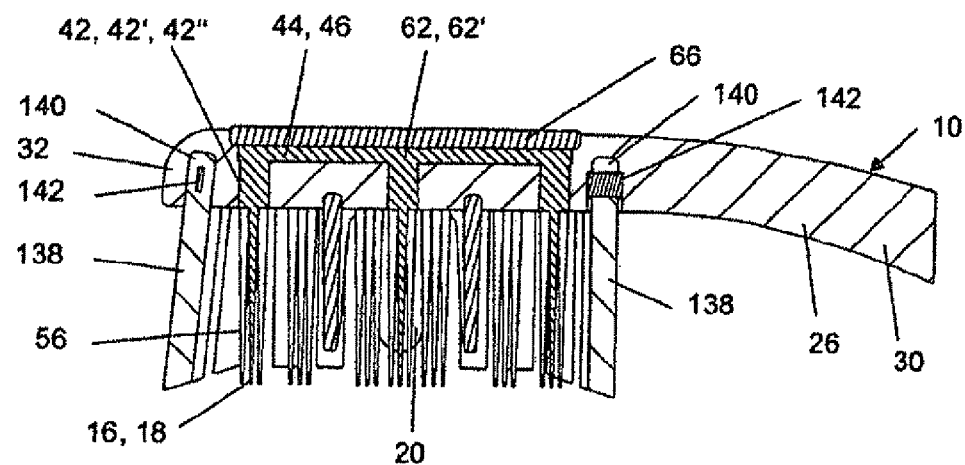
FIG. 63 shows a longitudinal section through the toothbrush according to FIGS. 61 and 62.

In addition, it is possible, as shown in FIGS. 61 to 63, to provide a toothbrush 10 as claimed in the present invention additionally with punched bristles 138. This is shown by the example of a toothbrush as claimed in the invention, analogous to the one according to FIGS. 27 to 44. On account of better readability, once again there will not be a complete description here and reference is made to the description of FIGS. 27 to 44.

First type injection-molded bristles 16 and/or, if needs be, second type injection-molded bristles 18 and, where applicable, the (bristle-free) flexible massaging and cleaning elements 20 are injected on the head part 32, i.e. onto the brush body 26 forming the bristle carrier 12, as is described and shown further above (in particular for FIGS. 27 to 44). In addition, however, when the brush body 26 is produced, blind holes 140 are realized in its head part 32 for the further bristle bundles 138 with extruded, conventional bristles 134, said further bristle bundles being bent in a U-shaped manner in a generally known way and fastened on the brush body 26 in said blind holes 140 by means of a wire anchor portion 142 by anchor punching.

In a preferred manner, the punching of the further bristle bundles 138 with extruded, conventional bristles 134 is effected after the injection molding of the injection-molded bristles 16 or 18 and of the (bristle-free) flexible massaging and cleaning elements 20. The blind holes 140 are preferably realized with the hard components of the handle part 28. In this case, the bristle material 62, 62' for the injection-molded bristles 16, 18 preferably does not form any part of the blind hole 140. The rear side of the head part 32 is preferably also free of bristle material 62, 62' behind the blind holes 140.

Only to complete the picture it must be mentioned that both in the case of the embodiment according to FIGS. 58 to 60 and in that according to FIGS. 61 to 63, it is possible to dispense with the massaging and cleaning elements 20.

At this point it must be mentioned that it is also possible, in the case of the embodiment shown in FIGS. 1 to 25, to provide in the head part 32 of the bristle carrier 12 blind holes 140 into which further bristle bundles 138 with extruded, conventional bristles 134 are punched in a known manner. To this end, it is possible, for example, to realize the part of the head part 32 extending around the small carrier plate 14 somewhat wider than shown and to realize a row of blind holes 140 there.

It is also conceivable to realize the small carrier plate 14 in a shorter manner, when viewed in the longitudinal direction of the toothbrush 10, and when viewed in the longitudinal direction, to provide the blind holes 140 for the further bristle bundles 138 with conventional, extruded bristles 134 in the head part 32 on the one side, on the other side or on both sides of the small carrier plate 14.

Figure 64:
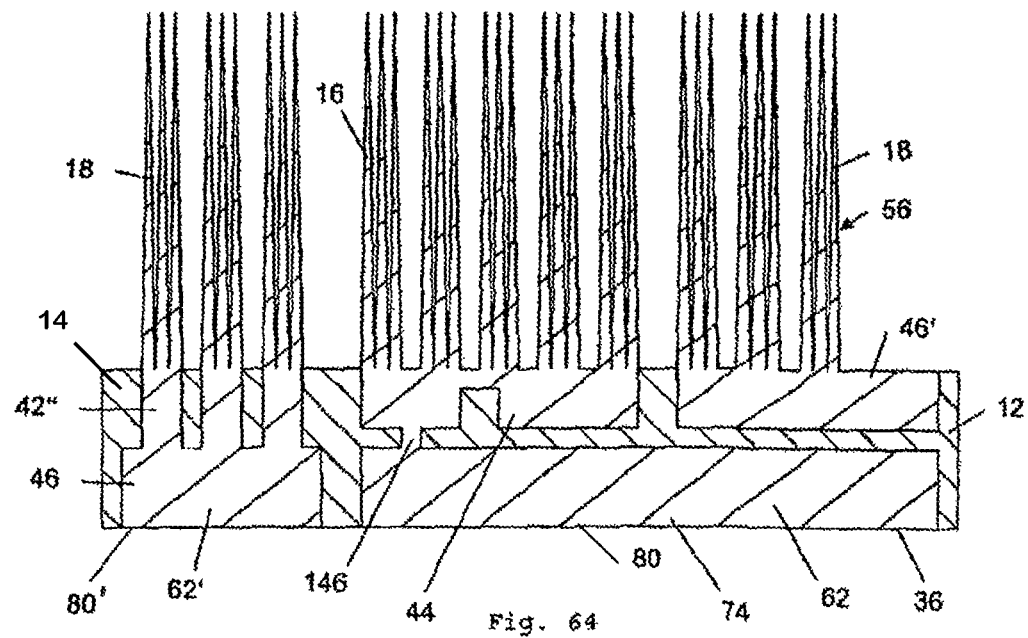
FIG. 64 shows a longitudinal section through a bristle carrier which is provided both on the front side and on the rear side with a distributing channel, or on the rear side with an injection channel for the bristle material.

As is shown in FIG. 64, it is also conceivable for the bristle carrier 12, be it the small carrier plate 14 or the brush body 26, to have on the rear side 36, 36' an injection channel 74 which is fluidically connected to the first distributing channel 44 on the front side 24 by means of an opening 146.

According to FIG. 64, the first type injection-molded bristles 16 are injected, as described further above, by the bristle material 62 being injected into the injection channel 74 at the injection point 80, said bristle material passing right through the opening 146 into the first distributing channel 44 for forming the first type injection-molded bristles 16.

It is also possible to provide the second distributing channel 46 on the rear side 36 and to produce the second type injection-molded bristles 18 right through the second passages 42", as is described in conjunction with the exemplary embodiment shown in FIGS. 1 to 25.

In the embodiment according to FIG. 64, however, there is a further second distributing channel 46' present on the front side 24 of the bristle carrier 12, said further second distributing channel 46' being fluidically connected to the second distributing channel 46. The further second distributing channel 46' can extend around the first distributing channel 44 on the front side 24 for this purpose and be connected to the second distributing channel 46 by means of a further opening 146.

For injection molding the second type injection-molded bristles 18, according to FIG. 64, the bristle material 62' is injected into the second distributing channel 46 at the injection point 80', from where it flows, on the one hand, through the second passages 42" and, on the other hand, through the relevant opening into the further second distributing channel 46' for forming the second type injection-molded bristles 18.

The exemplary embodiment shown in FIG. 64 shows that it is also possible to realize several bristle bundles 56 right through one single passage 42 or passage 146 by means of injection molding; i.e. to fill the cavities with bristle material for several bristle bundles.

The small carrier plate 14 from FIG. 64 has distributing channels 44, 46 both on the front side 24 and on the rear side 36'. The channels are shaped in the production process accordingly by both tool parts 82, 84 of the injection molding tool. In principle, the design is possible in three layers; first of all a distributing channel 44, 46 is realized from the rear side 36', a layer with the material of the small carrier plate 14 then follows and then, once again, a layer with distributing channels 44, 46 in which the injection-molded bristles 16, 18 are directly integrally molded.

The design of the small carrier plate 14 according to FIG. 64 results in different advantages and disadvantages. One advantage of the embodiment is that through the multiple-layeredness of the distributing channels, new more complicated arrangement possibilities are created for bristle bundles 56 and also for injection-molded (bristle-free) flexible massaging and cleaning elements 20. The distribution of the material in the small carrier plate 14 is also possible in a more complicated manner. It can be disadvantageous for the small carrier plate 14 to be thicker as a result of all the developments.

If the first type injection-molded bristles 16 and the second type injection-molded bristles 18 (in all embodiments) are not injected at the same time, the second channel wall 52 is acted upon with considerable pressure from the relevant first or second distributing channel 44, 46. In order to be able to absorb the resultant forces, the second channel wall 52 must be realized in a correspondingly sturdy, i.e. thick, manner. However, it is also possible to realize the second channel wall 52 thinner in this regard; so that the second channel wall 52 is not damaged, however, in the case of high injection pressures, it is to be supported in this case by means of the injection molding tool 60. This can be effected, for example, by means of a supporting geometry which engages in the second distributing channel 46 or first distributing channel 44.

In this case, it is possible to apply the so-called core-back technology. In this case, at the start of the injection molding cycle a core, that is a supporting geometry, is inserted into the corresponding distributing channel 44, 46 or the corresponding distributing channels and the first bristle material 62 is injected. The cores are then withdrawn and the further bristle material 62", for example for second type injection-molded bristles 18, is injected.

The time difference between the injection molding operations is between 0.5 s and 2.3 s, preferably between 1.2 s and 1.8 s. Said steps occur in the same cycle, the small carrier plate 14, or the bristle carrier 12, is not moved between the cycles.

If the first channel wall 50, as in the exemplary embodiments shown, is near the radially outside wall of the bristle carrier 12, a thin embodiment is possible if the carrier cavity 58 is realized in such a manner that it supports the bristle carrier 12 on the circumferential side.

The bristle carrier 12 according to FIG. 64 can have a second distributing channel 46 in addition to the first distributing channel 44.

Second passages 42" for the second type injection-molded bristles 18 can extend from the second distributing channel 46.

Finally regarding FIG. 64 it must be mentioned that it is possible to dispense with the distributing channels on the front or rear side of the bristle carrier 12 entirely, and consequently a cushion made of bristle material 62 can be formed which feeds several bristle bundles 56 and as a result is suspended flexibly inside the bristle carrier 12 or small carrier plate 14.

FIG. 65, which is enlarged compared to FIG. 55, shows a usage-side end portion of the bristle stem 103 of an injection-molded bristle 16, 18. The bristle cap 104 connects integrally to the usage-side end 103' of the bristle stem 103. The bristle cap 104, which in this case has a spherical form, in particular a hemispherical form, forms the usage-side end region by way of the usage-side end of the bristle 16, 18.

In place of the hemispherical bristle cap 104, the specially formed, usage-side end region 104' of the injection-molded bristle 16, 18 can also be realized in a conical manner or flatly with a rounded transition to the lateral surface of the bristle stem 103. It is equally conceivable to split the usage-side end region 104' of the bristle 16, 18 and thus to form an injection-molded bristle 16, 18 with several "ends".

All this is possible with a proposed injection molding tool by forming the second tool insert 100, the cap cavity 126, in a corresponding manner.

In addition, it is also conceivable to dispense with a specially formed usage-side end region 104' of the injection-molded bristles 16, 18 and to use the flat free end 103' of the bristle stem 103 as the usage-side end of the bristles 16, 18. In this case, the transition from the flat free end 103' to the lateral surface of the bristle stem 103 is sharp-edged. This can be realized in a simple manner with the proposed injection molding tool, by the second tool insert 100 being realized in a correspondingly flat manner.

The length of the bristle stem 103 is identified in FIG. 65 by way of the reference L, only the end region of said length on this side is shown and visible here, the other end is specified correspondingly in FIG. 66.

FIG. 66, which is enlarged compared to FIG. 55, shows in part two bristles 16, 18 at their exit from the bundle stem 130 by way of the bristle-body-side end 103". It can be seen particularly well that the injection-molded bristles 16, 18 are spaced apart from one another at their bristle foot at the bristle-carrier-side end 103".

As a representative example of all the embodiments, only FIGS. 54, 65, and 66 identify the diameters D, D1, the length L and the cone angle α of the bristle stem 103 in a corresponding manner.

A further embodiment of a manual toothbrush 10 as claimed in the present invention is explained in more detail by way of FIGS. 70-76.

Contrary to the embodiments already shown, the distribution of the material for the injection-molded bristles 16 is not effected exclusively by means of distributing channels 46 in the present embodiment. The distribution is effected for the most part in a flat manner, this means that the injection-molded bristles 16 emerge from a surface 148 with the bristle material 62.

The bristle carrier 12 in the head part 32 is realized integrally, in this case, with the neck part 30 and the handle part from a hard material using the injection molding method. The hard material forms the carrying, stabilizing frame of the manual toothbrush 10.

Obviously, a further material—hard material or soft material—can be injected in a known manner onto the hard material in the neck part 30 and/or handle part 28.

Figure 72:
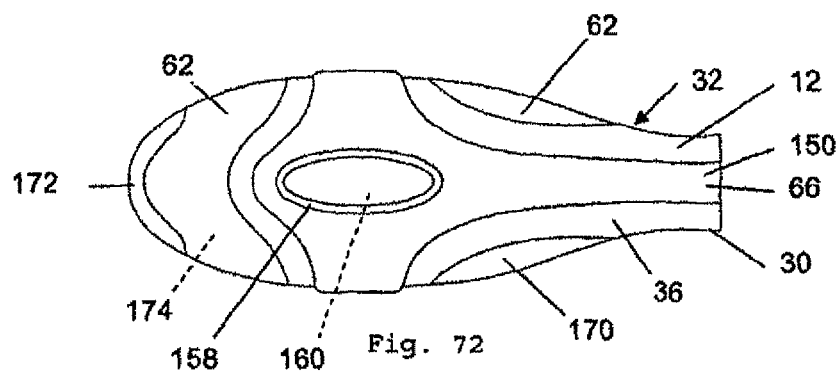
FIG. 72 shows a top view of the rear side of the head part and of the portion of the neck part of the toothbrush according to FIGS. 70 and 71.

In the exemplary embodiment shown, a feed channel 150 for supplying the soft material 66 for the flexible massaging and cleaning elements 20 from the neck part 30 into the head part 32 extends through the neck part 30, on the rear side 36; see FIGS. 72 and 75.

Figure 21:
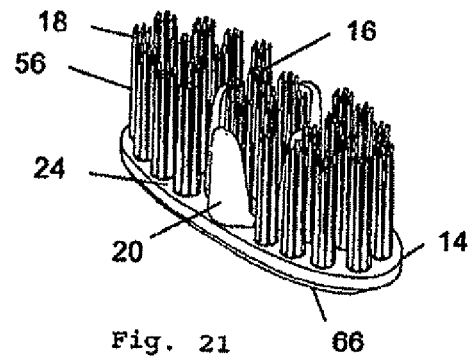
FIG. 21 shows the same representation as FIGS. 3, 9 and 15 of the small carrier plate from FIG. 20 provided with first and second type injection-molded bristles as well as additionally with flexible massaging and cleaning elements.
Figure 22:
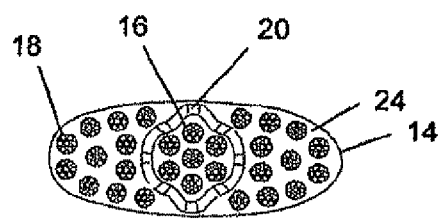
FIG. 22 shows the same representation as FIGS. 4, 10 and 16 of the small carrier plate from FIG. 20 provided with first and second type injection-molded bristles as well as additionally with flexible massaging and cleaning elements.
Figure 23:
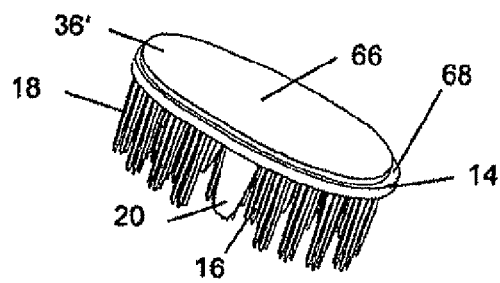
FIG. 23 shows the same representation as FIGS. 5, 11 and 17 of the small carrier plate from FIG. 20 provided with first and second type injection-molded bristles as well as additionally with flexible massaging and cleaning elements.
Figure 40:
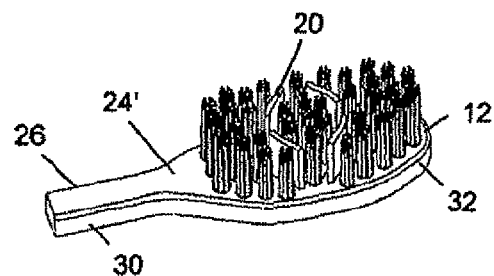
FIG. 40 shows the same representation as FIGS. 28 and 34 of the part of the toothbrush body provided with first and second type injection-molded bristles and flexible massaging and cleaning elements.
Figure 41:
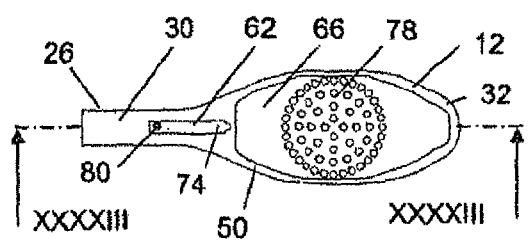
FIG. 41 shows the same representation as FIGS. 29 and 35 of the part of the toothbrush body shown there, the flexible material of the flexible massaging and cleaning elements covering the rear side of the toothbrush head and forming a tongue cleaning element.
Figure 42:
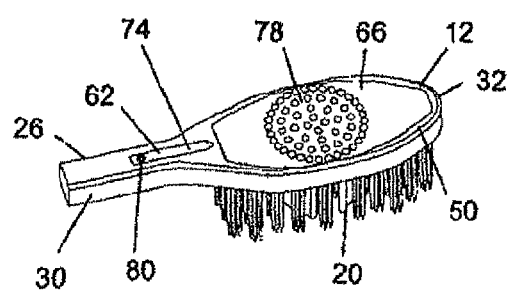
FIG. 42 shows the same representation as FIGS. 30 and 36 of the part of the toothbrush body with first and second type injection-molded bristles, flexible massaging and cleaning elements and the flexible tongue cleaning element.
Figure 43:
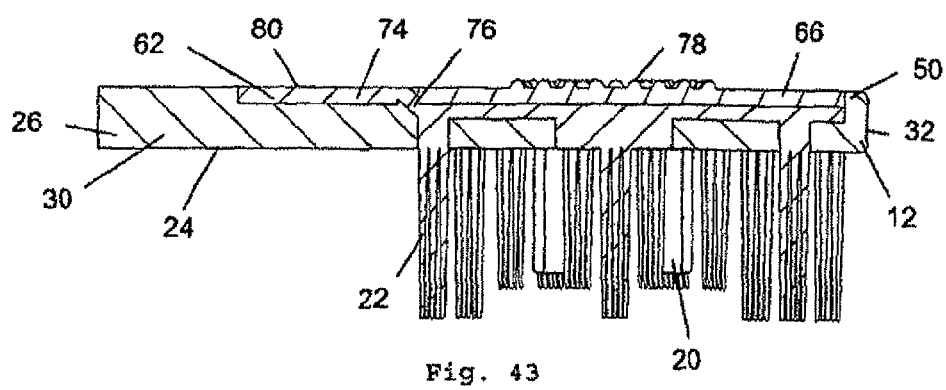
FIG. 43 shows a section along the line XXXXIII-XXXXIII of FIG. 41 of the part of the toothbrush body shown there, which is provided with first and second type injection-molded bristles, flexible massaging and cleaning elements and the flexible tongue cleaning element.
Figure 44:
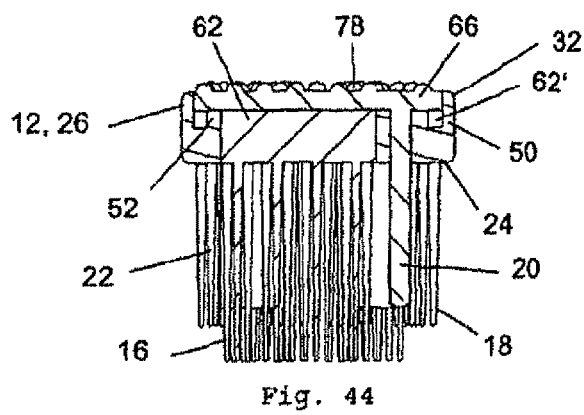
FIG. 44 shows a cross section along the line XXXXIV-XXXXIV of FIG. 39 of the part of the toothbrush body shown there, which is provided with first and second type injection-molded bristles, flexible massaging and cleaning elements and the flexible tongue cleaning element.

A, substantially triangular, soft material passage 152 extends from the front side 24' to the bottom of the feed channel 150 in the end region of the head part 32 facing the neck part 30. Said soft material passage is filled with the soft material 66 and the soft material forms (bristle-free) flexible massaging and cleaning elements 20 which protrude in relation to the front side 24'. In the exemplary embodiment shown, said elements are realized in a stem-like manner, with a circular cross section, tapering (lightly) toward the free end. However, they can also have other forms, for example as shown in FIG. 21 or 40.

A further field 154 of flexible massaging and cleaning elements 20 is provided on each side of the head part 32, approximately in the center of the head part 32 when measured in the longitudinal direction. At this location the bristle carrier 12 has a side recess 156, which is open toward the side, is continuous from the front side 24' to the rear side 36 and is connected to the feed channel 150 on the rear side 36; said feed channel extends on the rear side 36 in a cruciform manner—from the neck part 30—to the side recesses 156, it being defined centrally in the head part 132—in the crossing region—by an oval rib 158 of the bristle carrier 12.

The side recesses 156 are filled with the soft material 66, from the feed channel 150. Here too the bristle-free, flexible massaging and cleaning elements 20, which are injection-molded from the soft material 66, protrude in relation to the front side 24'. They are realized in a stem-like manner here, (lightly) tapering with a circular cross section.

The oval rib 158 defines a central passage 160, which extends from the rear side 36 to a large-area indentation 162 on the front side 24' of the bristle carrier 12. Said indentation 162 is defined on the side of the neck part 30 by a rib 164 of the bristle carrier 12 which defines the soft material passage 152 and at the side by arcuate ribs 166 which define the side recesses 156. Toward the exposed end of the head part 32, the indentation 162 is defined by a front wall 168 which extends in an undulating manner and is formed by the bristle carrier 12.

The bristle carrier 12 is realized set back in relation to the lateral outside edges of the head part 32 between the rib 164 and the ribs 166, as well between the latter and the front wall 168, such that the bristle material 62 is able to flow laterally around the bristle carrier 12 in these regions during injection molding; see in particular FIGS. 73 and 76.

The large-area indentation 162 is filled with the bristle material 62 such that this latter forms a surface covering on the bristle carrier 12, from which a plurality of bristle bundles 56 protrude with, seven in each case here, injection-molded bristles 16. These are realized integrally with the bristle material 66 which forms the surface covering.

For producing each of said bristle bundles 56, the relevant injection molding tool has first and second tool inserts 98, 100, as described further above and shown in FIG. 47-53 or 67-69.

As can be seen in particular from FIG. 72, the cruciform-shaped feed channel 150 which is filled with soft material 66 is defined on the rear side 36 with the hard material of the bristle carrier 12. On the other side—when viewed in the longitudinal direction between the arcuate ribs 166 and the rib 164—said rib-like boundary defines lateral regions 170 on the rear side 36 with bristle material 62.

The end of the feed channel 150 facing the free end of the head part 32 is defined by way of a further rib-shaped boundary of the bristle carrier 12, which extends in an undulating manner on the rear side 36—when viewed in the longitudinal direction—from the front end of the one rib 166 to the other.

Finally, the bristle carrier 12 has a protruding end rib 172 at the free end, on the rear side 36. Said rib, together with the above-mentioned further rib-like boundary, defines a channel-like indentation 174 which extends from the one side to the other and is also filled with the bristle material 62.

Passages 42, in this case four, extend from said channel-like indentation 174 to the front side 24' of the bristle carrier 12. Said passages are filled from the rear side 36 with the bristle material 62, forming four bristle stems 130. Said material also forms injection-molded bristles 16, in this case seven, per bristle stem 130, said injection-molded bristles protruding freely from the front side 24'.

Said passages 42 are located between the front wall 168 and the free end region of the head part 32.

All regions with bristle material 62 and all regions with soft material 66 are consequently separated from each other by means of the hard material of the bristle carrier 12. All regions with bristle material 62 are connected together and all regions with soft material 66 are connected together.

Obviously, it is also possible to realize a small carrier plate 14 (similar/or identical to the bristle carrier described above and shown in FIGS. 70-76) as the bristle carrier and to provide it in a corresponding manner with a surface layer 148 made of bristle material, by way of which injection-molded bristles or bristle bundles which protrude integrally therefrom are realized. Said small carrier plate 14 which is provided with the bristle material is fastened on the head part of the brush body, as described further above.

The embodiment shown in FIGS. 70 to 76 and described above is also suitable for an electric toothbrush.

The injection-molded bristles 16 which emerge from the surface 148, i.e. from the bristle material coating, are shown specifically with the bristle bundles 56 in the center of the head in FIGS. 70-76. The bristle material 62 is either injected directly in the head part 32 or is guided from the handle part 28 via the neck part 30 into the head part 32. In the present case, the injection point of the bristle material is provided directly in the head part 32. The bristle material 62 is distributed in the head part 32 such that it spreads out flatly and forms the injection-molded bristles 16 from said material spreading flatly. As a result, the surface between the relevant bristle bundles 56 is also formed to a large extent with the bristle material 62.

As well as this, it can also be seen in the said figures that (bristle-free) flexible massaging and cleaning elements 20 can be formed at the same time. These can be seen in FIG. 71 in the region of the transition between the neck part 30 and the head part 32 and, on the other hand, on the sides of the brush head in the fields 154 and side recesses 156. As an example, these are each in the form of a stem, but can obviously assume any forms which are able to be injection molded.

It can be seen in the front region of the head part 32 that bristle bundles 56 are formed and they are directly surrounded by the hard material of the bristle carrier 12. Said bristle bundles 56 are realized or formed with bristle material 62 from the rear side 36 of the toothbrush.

In the present example, the materials for the injection-molded bristles 16 and for the (bristle-free) flexible massaging and cleaning elements 20 are separated by hard material. This means that the toothbrush 10 is developed such that the injection-molded bristles 16 and also the flexible massaging and cleaning elements 20 can be injection-molded at the same time or slightly offset in time in the same injection molding cycle.

Figure 70:
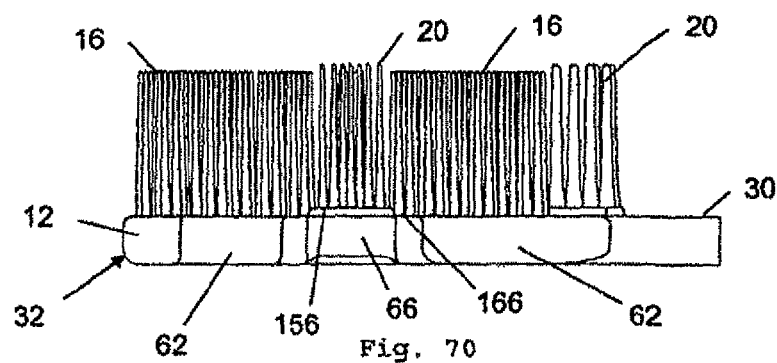
FIG. 70 shows a side view of the head part and of a portion connecting thereto of the neck part of a further embodiment of a toothbrush as claimed in the invention with injection-molded bristles and flexible massaging and cleaning elements.
Figure 71:
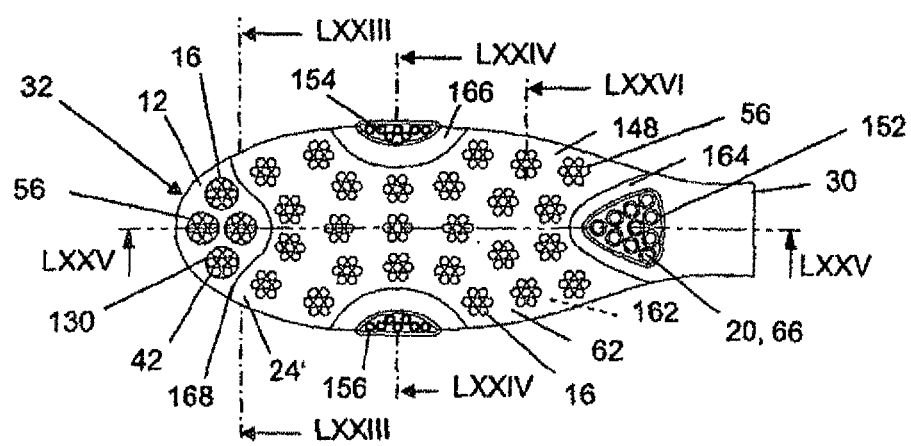
FIG. 71 shows a top view of the head part and of the portion of the neck part of the toothbrush according to FIG. 70.

FIGS. 73 to 76 show different sections through the head part 32 which is shown in FIGS. 70 to 72. They show, in particular, the distribution of the material and the connection possibilities between the different materials. The connection possibilities are important because the bristle material 62 does not connect every time to the material of the bristle carrier 12, i.e. a material bond is not necessarily produced during the injection molding process. Thus, in the case of many material combinations, positive locking is used in the design for the connection between the materials.

It can be seen from FIG. 73, a cross section in the front region of the head part 32, how the bristle material 62 forms around the bristle carrier 12. The bristle carrier 12 is formed from hard material and continues from the handle part 28 via the neck part 30 as far as up to the head part 32. It forms the stabilizing frame. The bristle material 62 wraps around the bristle carrier 12.

In this case, two possibilities for fixing are shown. On one hand, the bristle material 62 is wrapped around the bristle carrier 12 on both sides thereof, a clasping is achieved. In addition, the individual bristle bundle 56, which is supplied with bristle material 62 right through the bristle carrier 12, can be designed such that its bristle stem 130 extends right through a narrow point 176 and it is fixed in this manner on the bristle carrier. The bristle carrier 12 engages quasi in a circumferential groove of the bristle stem 130.

The widening of the passage 42 on the bristle side of the narrow point 176 is preferably between 0.05 mm and 0.3 mm, preferably between 0.08 mm and 0.15 mm. In this way, the bristle bundle 56 is not pressed rearward in use, the force is thus directed from the injection-molded bristles 16 via the bristle stem 130 onto the bristle carrier 12 and not onto the bristle material 62 on the rear side 36 of the head part 32.

FIG. 74 shows a center cross section through the bristle field, transversely with respect to the longitudinal axis of the toothbrush 10. In said example, all three materials present in said embodiment are shown. The bristle carrier 12 extends between the two materials, the bristle material 62 and the soft material 66 of the (bristle-free) flexible massaging and cleaning elements 20. The bristle material 62 extends along the inside of the body through the bristle carrier 12 and the soft material 66 is injected on the outside of the bristle carrier 12. It is easy to see in said cross section that the soft material 66 enters into a connection with the material of the bristle carrier 12, a hard material, during the injection molding process and consequently there is no need for positive locking connections. In the case of the bristle material 62, contrary to this, what happens is that said bristle material, as already shown in the example in FIG. 73, enters into positive locking with the bristle carrier 12. The positive locking is shown by means of an opening through the bristle carrier 12 and wider passages in front of and after the opening.

FIG. 75 shows a longitudinal section along the longitudinal axis of the toothbrush. It can be seen how the bristles protrude from the bristle material. This is shown in the center of the brush head. Once again, the positive locking theme is shown in the central region of the bristle field as well as in the front region of the brush head for the two bundles.

FIG. 76 shows that the bristle material 62 can also surround part of the bristle carrier 12 completely and thus is connected to said bristle carrier in a positive locking manner. This can also be realized by at least two openings 178 being realized side by side on the bristle carrier 12 and the bristle material 62 being distributed through both openings 178 and forming a unit in front of and after the openings 178. Or, as in the exemplary embodiment shown in FIG. 76, by one opening 178 being realized on the bristle carrier 12, close to the lateral edge, the bristle material 62 running right through the opening 178 and running laterally around the bristle carrier 12, as well as being connected on both sides of the opening 178 to form one unit. The minimum diameter of the opening 178 is between 0.3 mm and 1.4 mm, preferably between 0.5 mm and 1.0 mm.

Figure 78:
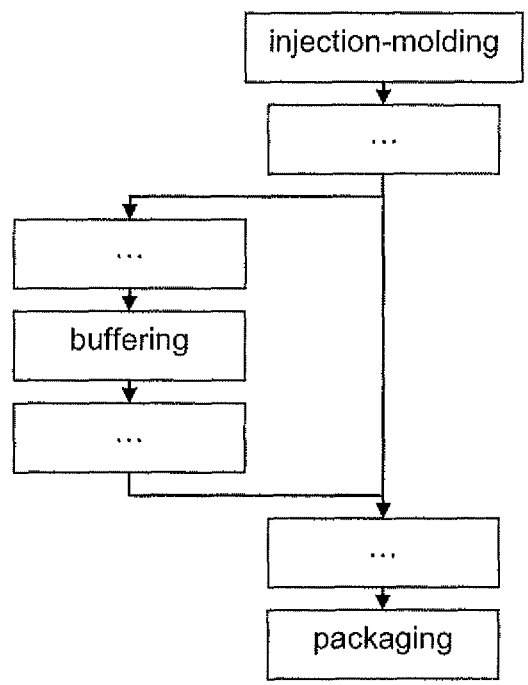
FIG. 78 shows a flow diagram for producing the completely packaged toothbrush using the inline method.

The head part 32, shown in FIGS. 70-76, of a manual toothbrush 10 is designed such that it can be produced in a very efficient manner in a cubed tool. The corresponding flow diagram is shown in FIG. 78.

In the first step, that is to say in the first station of the four stations of the cubed tool, the basic body is produced by means of injection molding. Said basic body corresponds to a large extent to the brush body 26 of the finished manual toothbrush 10. The basic body consists in the majority of cases of a hard material which ensures the basic stability of the final product or to a great extent forms the brush body 26.

A cooling operation which allows the basic body to cool down at least in part takes place in the second station of the cubed tool. However, it is also possible for further manipulations to be effected on the basic body in said station. For example, the attaching of assembly parts, identifications, etc.

The injection-molded bristles 16 are provided in the third station, once again by means of injection molding. The manual toothbrush 10 shown includes only one type of injection-molded bristles 16 which are provided in this case. As well as this, a further material component which forms part of the handle and also part of the rear side 36 of the head part 32 of the toothbrush 10 is also provided in the third station. In the exemplary embodiment shown, it consists of the soft material 66 and forms the (bristle-free) flexible massaging and cleaning elements 20.

This is possible because the hollow spaces for the different materials are separated on the bristle carrier 12 and thus it is possible to insert the different materials in a parallel manner.

It is also possible for several types of injection-molded bristles to be injection-molded in the third station. In this case, it is necessary, as described above, for the different material components to be completely separated from one another. Thus, for example, alongside first type injection-molded bristles 16 second type injection-molded bristles 18 or the flexible massaging and cleaning elements 20 can be injection-molded.

It is advantageous for the rational production of the manual toothbrush 10 for the product to have run through the complete injection molding process after the injection molding in the third station. Further volumes on the brush body 26 can nevertheless still be attached later, for example by assembly. In this case, volumes can be bonded, clicked-in, welded-on, etc.

The brush bodies 26 are removed in the fourth station of the cubed tool.

A great advantage of the production of the manual toothbrushes 10 in this manner is that the costly cavities for the production of the injection-molded bristles, that is to say the first and second tool inserts 98, 100, only have to be produced for one single station as no further manipulations have subsequently to be provided for the bristle field by means of injection molding. In addition, after said interlinked steps the product is completely or largely completed.

The most rational production is achieved by directly or indirectly linking the injection molding process to the following processes. This is shown in the flow diagram in FIG. 76. Obviously, said interlinking does not necessarily have to be adopted.

In this case, the procedure is such that the manual toothbrush 10, directly it comes out of the injection molding process, is processed further, that is to say is packaged. In this case, it is possible for different additional processing processes to be performed on the manual toothbrush 10 before it is finally packaged. As well as this, it is also possible for the manual toothbrushes 10 to be buffered.

The additional processing processes, in this case, can take place before or after the buffering or even along the direct path from the injection molding to the packaging. Said process steps are symbolized by Examples of processing operations which can take place in said steps are embossing (identifying or decorating), providing with the batch number and so on.

The buffer, which is preferably present, serves to give the two processes of injection molding and packaging, in spite of the interlinking, a certain independence. As shown in the flow diagram, it is possible to use such a buffer or not to use one.

Packaging is effected at the end of the production chain. In this case, the manual toothbrush 10 is wrapped around with packaging. Examples of this are blister packaging, bag packaging, etc.

The statements made in conjunction with the individual bundles 128 and their bristles 16, 18 also refer in a corresponding manner to the embodiments described further above with bristle bundles 56 with injection-molded bristles 16, 18; the bristle base 64 then corresponds to the bundle stem 130.

In order to develop toothbrushes 10 in a more effective manner, it is also possible to bestow more abrasiveness on the bristle material 62, 62' and/or the soft material 66. Grinding particles can be incorporated into the plastics material for this purpose.

In addition, it is possible to add particles for decoration and shaping, for example glitter particles, in order to obtain a visual effect in this manner.

Using the described preferred development variants for injection-molded bristles 16, 18, it is possible to meet the demands made on bristle bundles. They are to be as abrasion-resistant as possible, to have good resistance to chemicals, to be stable or to have good resetting ability and are also not to be easily torn out.

The resistance to chemicals is measured using the so-called Odol test (Odol is a trademark of SmithKline Beecham Consumer Healthcare GmbH). In this case, the brush head is inserted into a solution consisting of 50% Odol and 50% water for 24 hours. The damage to the material and the discoloration are then assessed, that is to say the appearance and the functionality are tested.

The strength and the resetting ability are assessed as a result of a scrubbing movement on a tooth structure for 13.5 hours at a load of 250 grams. The visual appearance of the bristle field is the assessment criterion.

The pull-out weight of the bristle bundles is assessed by way of precise measuring. To this end, a bristle bundle is clamped and pulled away from the fixed brush head. The pull-out weight, in this case, must be at least 1.8 kg.

Figure 77:
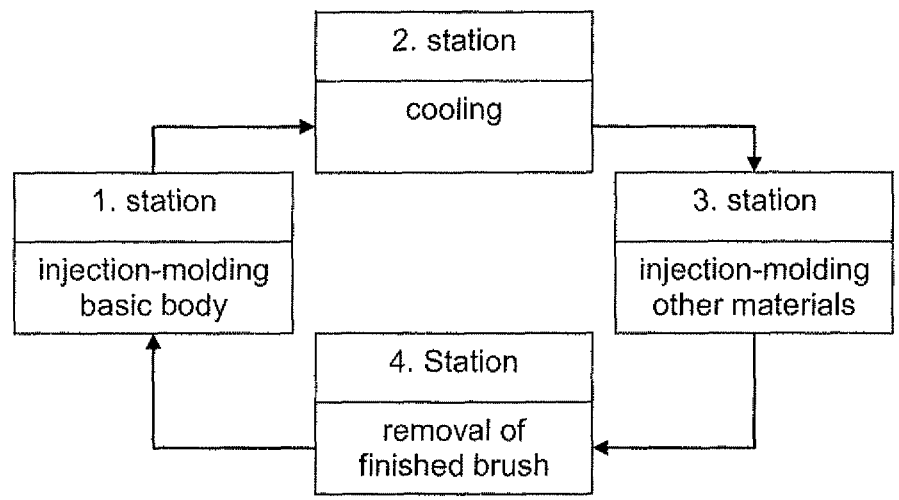
FIG. 77 shows a flow diagram for producing a toothbrush as claimed in the invention in a cubed tool.

The production method shown in FIGS. 26, 45, 77 and can, as described, have different process steps downstream, such as, for example, packaging.

In this case, it is also possible to finish the injection-molded bristles 16, 18 and in this way to exclude limitations which are provided by the injection molding process. Thus, the injection-molded bristles 16, 18, for example in an analogous manner to the extruded conventional bristles 134, can be cut and rounded. In this respect, the bristle materials 62, 62' play a central role and have to allow the treatment. This is to say, for example, that they must not melt as a result of the rounding process or are only allowed to melt in a very controlled manner.

The method steps downstream, which are addressed in conjunction with FIGS. 26, 45, 77 and 78, and also the method steps shown in each case can be directly linked in the production process such that, for example, finished packaged toothbrushes are ejected at the end of the production line, i.e. the production is effected inline, that is without the process steps carried out being separated in any way.

Different numbers of injection molding machines are required for the production of the toothbrushes, that is for the injection molding, depending on the design.

At least two injection molding machines are required for the production of a toothbrush 10 with a brush body 26 and a small carrier plate 14 with injection-molded bristles 16, 18 according to FIGS. 2 to 25 and as shown in FIG. 26. A first machine in order to produce the brush body 26 and a second machine to produce the small carrier plate 14 and to inject the injection-molded bristles 16, 18 and the (bristle-free) flexible massaging and cleaning elements 20. Depending on the design of the production process and of the toothbrush 10, a further injection molding machine is required for joining the small carrier plate 14 and the brush body together or said step is incorporated into one of the existing injection molding machines or the joining together does not take place by means of injection molding.

At least one injection molding machine is required for the production of a toothbrush 10 with a brush body 26, the head part 32 of which forms the bristle carrier 12, and with injection-molded bristles 16, 18 as well as flexible massaging and cleaning elements 20, as shown in FIGS. 27 to 45. The production can be effected in one single injection molding tool on an injection molding machine. It can also be possible by way of process control for the production to be divided up and, for example, the brush body 26 to be produced on one machine and the injection-molded bristles 16, 18 as well as the flexible massaging and cleaning elements 20 to be injected on another machine.

The tool technology or the tool technologies which are used or can be used for producing the toothbrushes 10 are all known, from stack-type tools, via cubed tools, via index plate tools and helicopter tools through to SPCS tools. In this case, it is also possible to develop tools in a simple manner and to do without robot aids for moving the parts and to perform this manually.

Obviously, the development variants shown are examples and the individual definitions and elements of said development variants can be combined with other development variants without departing from the framework of said invention. In particular, the arrangements of the bristles, soft elements, channels and passages are to be seen as examples and can take place in other arrangements.

The descriptions given for specific figures can obviously also be transferred to other figures which show the same or similar definitions and in which the definitions are not described in the same detail.

To complete the picture, it must be mentioned that the disclosure in conjunction with the injection-molded bristles 16, 18 and bristle bundles 56 or individual bundles 128 is also applicable if the distributing channels 44, 46 are situated on the front side of the bristle carrier 12 and the injection-molded bristles 16, 18 protrude in said distributing channels directly from the bristle material 62, 62'. Said bristle material 62, 62' then forms the bristle base 64 or the bundle stem 130.

The invention claimed is:

1. A toothbrush having a bristle carrier with a front side and a rear side, which is produced using the injection molding method and having injection-molded bristles which protrude from the bristle carrier, are produced from a bristle material using the injection molding method and have a bristle stem,
   wherein the bristle carrier has on its rear side at least one channel-like indentation for the bristle material, and a number of the injection-molded bristles are realized integrally with the bristle material in the channel-like indentation,
   wherein the bristle carrier has on its front side a surface layer produced from the bristle material and wherein further injection-molded bristles are realized integrally with the surface layer and protrude from said surface layer.

2. The toothbrush as claimed in claim 1, wherein the ratio between the diameter of the injection-molded bristles, measured at a usage-side end of the bristle stem, and the exposed length of the injection-molded bristles is at least 1:35.

3. The toothbrush as claimed in claim 2, wherein the ratio between the diameter of the injection-molded bristles and the exposed length is a maximum of 1:90.

4. The toothbrush as claimed in claim 1, wherein the diameter of the injection-molded bristles on a bristle-carrier-side end is between 0.5 and 1 mm.

5. The toothbrush as claimed in claim 1, wherein the exposed length of the injection-molded bristles is between 4 mm and 16 mm.

6. The toothbrush as claimed in claim 1, wherein the injection-molded bristles have a minimum cone angle of between 0.5° and 5°.

7. The toothbrush as claimed in claim 1, wherein the injection-molded bristles on a usage-side end of the bristle stem, connecting thereto in an uninterrupted manner, have a specially formed, usage-side end region.

8. The toothbrush as claimed in claim 1, wherein the at least one channel-like indentation, on the rear side of the bristle carrier facing away from the injection-molded bristles, is realized on said bristle carrier and the bristle carrier has passages for the bristle material which extend from the bottom of the channel-like indentation to a front side of the bristle carrier facing the injection-molded bristles.

9. The toothbrush as claimed in claim 8, wherein one passage has associated therewith several injection-molded bristles.

10. The toothbrush as claimed in claim 9, wherein the injection-molded bristles are associated with one single passage form a bristle bundle.

11. The toothbrush as claimed in claim 10, comprising between 20 and 50 bristle bundles with injection-molded bristles.

12. The toothbrush as claimed in claim 10, wherein the injection-molded bristles in each case forming a bristle bundle converge toward one another toward the usage-side end.

13. The toothbrush as claimed in claim 9, wherein the number of injection-molded bristles associated with one single passage is between 2 and 15.

14. The toothbrush as claimed in claim 9, wherein the bristle material in the region of the passage forms a bristle base which is common to the injection-molded bristles associated with the passage.

15. The toothbrush as claimed in claim 9, wherein the bristle material, in the region of the passage and opposite the front side of the toothbrush, forms a bristle base which is common to the injection-molded bristles associated with the passage.

16. The toothbrush as claimed in claim 8, wherein an injection point for the bristle material, arranged offset with reference to the passages, is positioned in the vicinity of the edge of the bristle carrier, outside the zone with the passages.

17. The toothbrush as claimed in claim 1, comprising between 100 and 500 injection-molded bristles.

18. The toothbrush as claimed in claim 1, wherein at least one bristle-free, flexible massaging and cleaning element is injected on the bristle carrier and said element consists of a soft material.

19. The toothbrush as claimed in claim 18, wherein the soft material is at least one selected from the group consisting of thermoplastic polyurethane elastomer (TPE-U), thermoplastic styrene elastomers (TPE-S), thermoplastic polyamide elastomer (TPE-A), thermoplastic polyolefin elastomer (TPE-O), thermoplastic polyester elastomers (TPE-E), thermoplastic polyethylene (PE) and polyurethane (PU), and the hardness of the soft material is less than 90 Shore A.

20. The toothbrush as claimed in claim 18, wherein the soft material for the bristle-free, flexible massaging and cleaning elements has a hardness of less than 40 Shore A.

21. The toothbrush as claimed in claim 18, wherein the Shore A hardness of the soft material for the bristle-free, flexible massaging and cleaning element is lower than the Shore A hardness of the bristle material for the injection-molded bristles.

22. The toothbrush as claimed in claim 1, further comprising a bristle-free, flexible tongue cleaning element which consists of a soft material.

23. The toothbrush as claimed in claim 1, wherein the bristle carrier consists of at least one hard material and the bristle material differs from the hard material.

24. The toothbrush as claimed in claim 23, wherein the bristle material is fastened on the bristle carrier in a mechanical manner.

25. The toothbrush as claimed in claim 23, wherein the hard material for the bristle carrier comprises at least one of the following thermoplastics selected from the group consisting of: styrene polymer; polyolefin; polyester; cellulose derivative; polyamides (PA); polymethyl methacrylate (PMMA); polycarbonate (PC); polyoxymethylene (POM); polyvinyl chloride (PVC); and polyurethane (PUR).

26. The toothbrush as claimed in claim 1, wherein the bristle material is a polyamide elastomer, a polyester elastomer or a hard material.

27. The toothbrush as claimed in claim 1, wherein the bristle material has a hardness of between 30 and 80 Shore D.

28. The toothbrush as claimed in claim 1, wherein the bristle carrier is connected to an electric drive element and can be set into an oscillating, pivoting or translatory movement.

29. The toothbrush as claimed in claim 28, wherein the bristle carrier is connected to a neck part and the neck part can be fitted onto a handle part with the drive element.

30. The toothbrush as claimed in claim 28, wherein the bristle carrier is driven at a movement frequency of between 6,000 and 20,000 movement cycles per minute.

31. The toothbrush as claimed in claim 28, wherein a path covered by usage-side ends of the injection-molded bristles, per movement cycle, is smaller than 5 mm.

32. The toothbrush as claimed in claim 1, wherein the length of an exposed part of the injection-molded bristles corresponds to the length of the bristle stem or is longer by a maximum of 10%.

33. A method for producing a toothbrush as claimed in claim 1, where a bristle carrier and injection-molded bristles, which are made from a bristle material, protrude from the bristle carrier and have a bristle stem, are produced using the injection molding method, wherein at least one channel-like indentation is realized on the rear side of the bristle carrier for the bristle material and at least a number of the injection-molded bristles are realized integrally with the bristle material in the channel-like indentation.

34. A toothbrush, comprising:
a bristle carrier with a front side and a rear side that is produced using the injection molding method; and
injection-molded bristles that are produced from a bristle material using the injection molding method and have a bristle stem,
wherein the bristle carrier has a surface layer integrally molded from the bristle material on the front side of the bristle carrier and connected by passages through the bristle carrier to the rear side of the bristle carrier, and
wherein the injection-molded bristles are connected to and protrude from the surface layer on the front side of the bristle carrier.

35. A toothbrush, comprising:
an injection-molded bristle carrier with a front side and a rear side and being made of a hard material; and
injection-molded bristles that are made from a bristle material being softer than the hard material of the bristle carrier and the bristle material being mechanically, non-releasably connected by means of positive locking to the bristle carrier without forming a material bond with the hard material of the bristle carrier,
wherein the bristle material forming a surface layer is integrally molded on the front side and on the back side of the bristle carrier and is connected by passages in the bristle carrier, and
wherein the injection-molded bristles protrude from the front side of the bristle carrier.

* * * * *